(12) United States Patent
Nagel et al.

(10) Patent No.: US 12,226,167 B2
(45) Date of Patent: Feb. 18, 2025

(54) SYSTEMS AND METHODS FOR USE WITH MRI-GUIDED FOCUSED ULTRASOUND

(71) Applicant: The Cleveland Clinic Foundation, Cleveland, OH (US)

(72) Inventors: Sean J. Nagel, Cleveland Heights, OH (US); Mark D. Bain, Cleveland, OH (US); Stephen Jones, Cleveland Heights, OH (US); Shengqiang Gao, Beachwood, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 212 days.

(21) Appl. No.: 17/868,282

(22) Filed: Jul. 19, 2022

(65) Prior Publication Data
US 2023/0017864 A1    Jan. 19, 2023

Related U.S. Application Data

(60) Provisional application No. 63/223,361, filed on Jul. 19, 2021.

(51) Int. Cl.
*A61B 34/20* (2016.01)
*A61B 17/22* (2006.01)
(Continued)

(52) U.S. Cl.
CPC .......... *A61B 34/20* (2016.02); *A61B 17/2202* (2013.01); *G01R 33/4812* (2013.01); *A61B 2017/22079* (2013.01); *A61B 2017/22082* (2013.01); *A61B 2034/2051* (2016.02); *A61B 2090/3762* (2016.02); *A61M 25/0026* (2013.01); *A61M 2025/0681* (2013.01)

(58) Field of Classification Search
CPC ...... A61B 17/2202; A61B 2017/22079; A61B 2017/22082; A61B 34/20; A61B 2034/2051; A61B 2090/3762; A61M 25/0026; A61M 2025/0681; G01R 33/4812
See application file for complete search history.

(56) References Cited

U.S. PATENT DOCUMENTS

| | | |
|---|---|---|
| 5,613,954 A | 3/1997 | Nelson et al. |
| 5,697,946 A | 12/1997 | Hopper et al. |

(Continued)

FOREIGN PATENT DOCUMENTS

WO    1998051214    11/1998

OTHER PUBLICATIONS

Manish Ranjan, Alexandre Boutet, Sanjiv Bhatia, Angus Wilfong, Walter Hader, Mark R Lee, Ali R Rezai & P. David Adelson (2019) Neuromodulation beyond neurostimulation for epilepsy: scope for focused ultrasound, Expert Review of Neurotherapeutics, 19:10, pp. 937-943, Jul. 2, 2019.

(Continued)

*Primary Examiner* — Chao Sheng
(74) *Attorney, Agent, or Firm* — Tucker Ellis LLP

(57) ABSTRACT

Systems and methods for sonicating a body within an organ of a patient include supplying ultrasound energy to the body in order to produce a liquified material, which can then be aspirated from the body via a catheter. Image guidance is used during aspiration of the liquified material.

27 Claims, 20 Drawing Sheets

(51) Int. Cl.
*G01R 33/48* (2006.01)
*A61B 90/00* (2016.01)
*A61M 25/00* (2006.01)
*A61M 25/06* (2006.01)

(56) References Cited

U.S. PATENT DOCUMENTS

| | | | |
|---|---|---|---|
| 2007/0060884 A1 | 3/2007 | Hayek | |
| 2007/0225643 A1* | 9/2007 | Hopper | A61M 25/04 604/103.05 |
| 2012/0078140 A1 | 3/2012 | Nita | |
| 2018/0154186 A1 | 6/2018 | Xu et al. | |
| 2019/0021666 A1* | 1/2019 | Hynynen | A61B 5/4064 |
| 2019/0133620 A1 | 5/2019 | Giese et al. | |
| 2019/0366123 A1 | 12/2019 | Adler et al. | |
| 2020/0352473 A1* | 11/2020 | Chen | A61B 5/0022 |
| 2020/0360733 A1* | 11/2020 | Yan | A61N 7/02 |
| 2024/0057967 A1* | 2/2024 | Treeby | A61B 8/4281 |

OTHER PUBLICATIONS

Chapman, Martin, et al. "Anesthesia considerations of magnetic resonance imaging-guided focused ultrasound thalamotomy for essential tremor: a case series." Canadian Journal of Anesthesia. vol. 67. Apr. 14, 2020. pp. 877-884.

International Search Report & Written Opinion issued in corresponding PCT patent application No. PCT/US2022/037585 dated Jan. 13, 2023, 19 pages.

Looi, Thomas, Karolina Piorkowska, Charles Mougenot, Adam Waspe, Kullervo Hynynen, and James Drake. "An MR-based quantitative intraventricular hemorrhage porcine model for MR-guided focused ultrasound thrombolysis." Child's Nervous System 34, No. 9 (2018): 1643-1650.

Prada, Francesco, M. Yashar S. Kalani, Kaan Yagmurlu, Pedro Norat, Massimiliano Del Bene, Francesco DiMeco, and Neal F. Kassell. "Applications of focused ultrasound in cerebrovascular diseases and brain tumors." Neurotherapeutics 16, No. 1 (2019): 67-87.

Min, Byoung-Kyong, Alexander Bystritsky, Kwang-Ik Jung, Krisztina Fischer, Yongzhi Zhang, Lee-So Maeng, Sang In Park, Yong-An Chung, Ferenc A. Jolesz, and Seung-Schik Yoo. "Focused ultrasound-mediated suppression of chemically-induced acute epileptic EEG activity." BMC neuroscience 12, No. 1 (2011): 23.

Monteith, Stephen, Jason Sheehan, Ricky Medel, Max Wintermark, Matthew Eames, John Snell, Neal F. Kassell, and W. Jeff Elias. "Potential intracranial applications of magnetic resonance-guided focused ultrasound surgery: a review." Journal of neurosurgery 118, No. 2 (2013): 215-221.

* cited by examiner

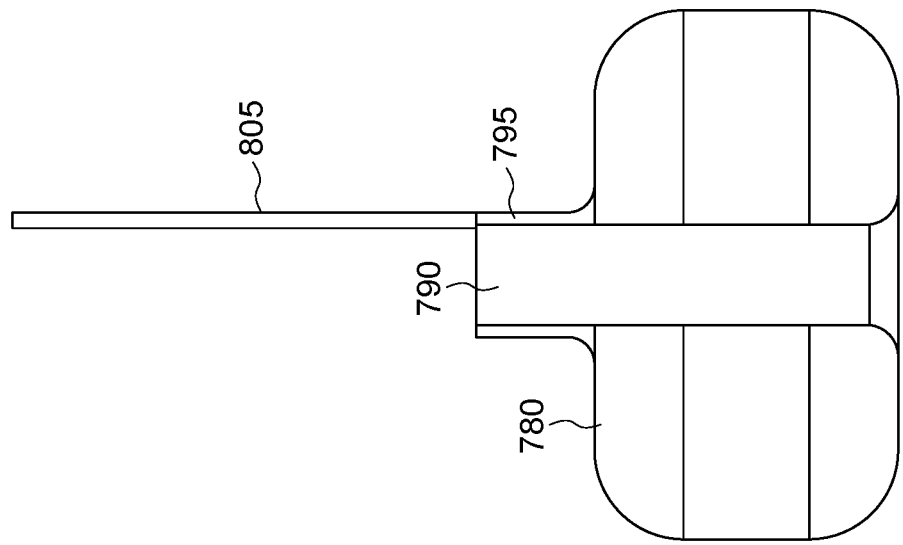
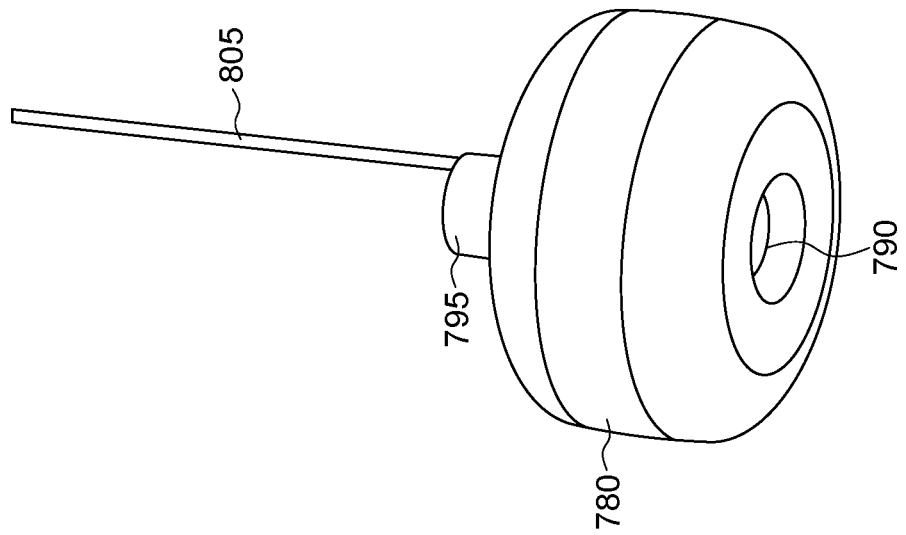
FIG. 8B
FIG. 8A

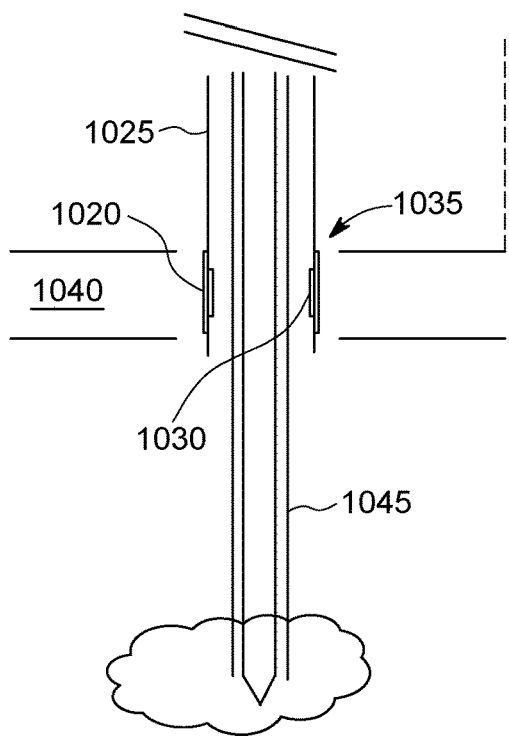
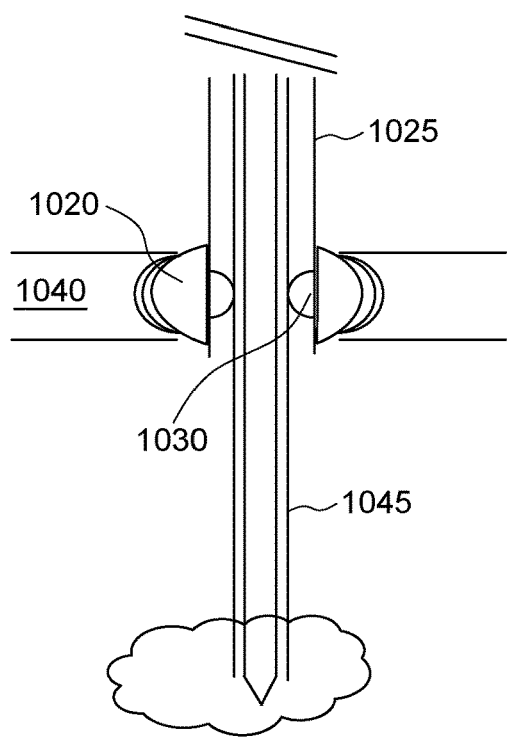
FIG. 12A
FIG. 12B
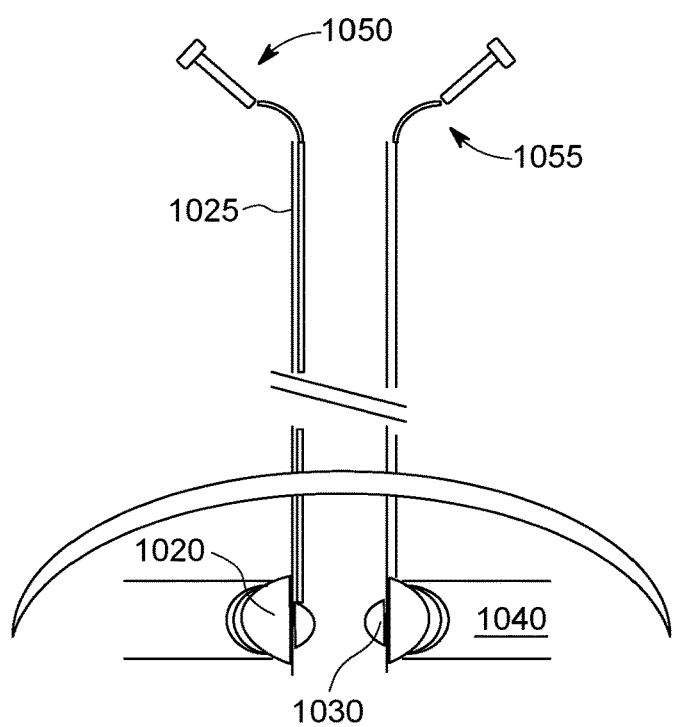
FIG. 13

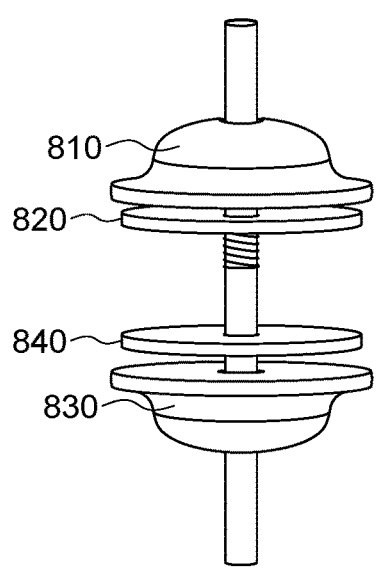 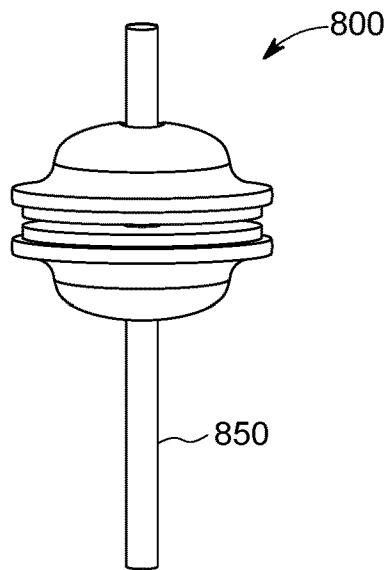
FIG. 16A  FIG. 16B
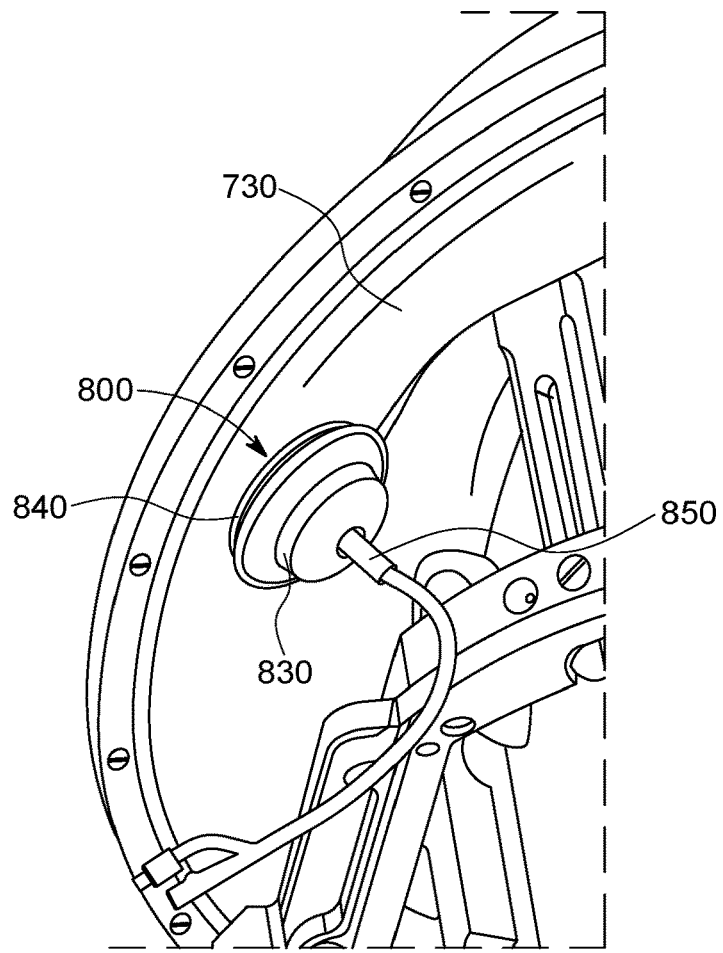
FIG. 17

SYSTEMS AND METHODS FOR USE WITH MRI-GUIDED FOCUSED ULTRASOUND

This application claims priority to and any other benefit of U.S. Provisional Patent Application Ser. No. 63/223,361 filed Jul. 19, 2021, the contents of which are incorporated herein in their entirety by reference.

TECHNICAL FIELD

The present invention relates to systems and methods for use with MRI-guided focused ultrasound.

BACKGROUND

Deep brain hemorrhages are a major cause of disability and death worldwide. Depending on their size and location, they may be untreatable due to higher risk associated with removal, and as a result the outcomes are often devastating. For example, available surgical treatments cause widespread collateral damage to healthy brain tissue because a large window is needed for access to drain the hematoma.

Parenchymal intracranial hemorrhage (ICH) occurs in both superficial and deep regions of the brain, often extending across these boundaries, and sometimes into the adjacent ventricle. Depending on the size, location, patient symptoms, and elapsed time after the hemorrhage, direct surgical evacuation of the clot may be included in the recommended treatment plan. For others, aggressive critical care including cardiovascular and respiratory support, intracranial pressure management and reversal of coagulopathies forms the core of medical care. Furthermore, the heterogeneity of the location and premorbid state for these patients complicates decision making and outcome measures. Thus, standardized care for this disease, despite its prevalence remains elusive.

Multiple studies have investigated the role of surgery to evacuate brain hemorrhages. Patients with an ICH volume over 30 cc are statistically correlated with poor outcome as the increased intracranial pressure reduces cerebral perfusion. Patients with hematoma volumes over 60 cc on CT have a predicted 30-day mortality over 90%; and volumes more than 150 cc usually lead to death due to decreased cerebral blood flow below the critical level. The high rate of disability or death after surgery for any volume ICH has raised question about this approach, especially for deep hemorrhages. To access and evacuate a deep clot requires an open craniotomy. This traditionally includes the removal of a large bone flap and the open dissection and retraction of normal brain tissue to reach the hemorrhage location. In a meta-analysis study, most open surgeries showed no definitive clinical benefit for patients with ICH. Visualization is often compromised and even the safest corridor still will injure normal brain. Recently, with these principals in mind, minimally invasive systems signify we may be at a transition point in treatment. Minimally invasive procedures without using thrombolytic drugs have demonstrated positive impact on patient's overall outcome if the hemorrhage was around 25-40 cm$^3$ with good clinical status (Glasgow Coma scale≥9). The evidence suggests that new devices should focus on removing the ICH through the smallest possible evacuation catheter. However, most of the minimally invasive systems now available for clinical use are poorly suited to the task, requiring a large bore guide tube. An ideal solution would include an evacuation channel no larger than a standard drainage catheter, of about several millimeters. But these two goals are at odds with one another as small channels are poorly suited to draining thick clots with viscoelastic properties that resist negative pressure aspiration.

Magnetic resonance-guided focused ultrasound (MRgFUS) is an FDA approved device that creates a focal thalamic lesion in the brain to treat upper extremity tremor in patients who are either not candidates for deep brain stimulation or are unwilling to undergo an open surgical procedure. The MRgFUS procedure is incisionless. A head frame is used to hold the patient's head motionless, and a focused ultrasound device is situated several centimeters from the scalp, with the intervening space filled with chilled water (as a medium to conduct ultrasonic waves and remove generated heat from the scalp) contained by a watertight, elastic membrane that is applied circumferentially about the patient's head.

The focused ultrasound device in the conventional setup comprises 1024 transducers mounted in a helmet apparatus that fits over the elastic membrane holding the ultrasound medium (water). The array of transducers is used to focus ultrasound energy to a focal spot only 6 mm in diameter to heat neural tissue to denature proteins (typically >55 C) and cause a rapid coagulative necrosis. This selectively 'lesions' the brain. The focal spot is identified (and treatment progress is tracked) via magnetic resonance imaging (MRI) guidance. Treatment of essential tremor (ET) and tremor-dominant Parkinson's disease (PD) were the first FDA-approved indications for MRgFUS. Use of this technology to treat other neurological conditions also would be desirable.

Multiple studies have confirmed that clotted blood is liquified when sufficient ultrasound energy is delivered. Thus, treating parenchymal (e.g. deep-brain) hemorrhages is a potential application for MRgFUS. However, the conventional configuration of MRgFUS for treating tremor is insufficient for treating hemorrhages, for example because it provides no mechanism to access and drain (aspirate) liquefied hemorrhage material simultaneously. Accordingly, there is a need for catheters and related tools that can be temporarily inserted to drain (e.g. intracranial) the liquefied blood clot when using an MRgFUS system. In particular the catheter and related tools would not interfere with or damage the MRI equipment while in-use to provide image guidance for focused ultrasound treatment (liquefaction) of the hemorrhage.

SUMMARY

According to one embodiment, a method of treatment is provided. The method includes sonicating a body within an organ of a patient with ultrasound energy thereby liquefying the body to produce liquified material and aspirating the liquified material via a catheter positioned adjacent to or within the body, wherein both sonication of the body and positioning of the catheter adjacent thereto are assisted via image guidance.

According to another embodiment, a system to facilitate magnetic resonance-guided focused ultrasound aspiration is provided. The system includes: a transducer assembly comprising an array of ultrasound transducers adapted to deliver ultrasound energy, said transducer assembly at least partially defining a substantially liquid-tight jacket adapted to contain a fluid medium in order to conduct ultrasound waves; and an access port adapted to accommodate therethrough a guide tube emerging from said jacket; wherein said guide tube is made exclusively of substantially non-ferromagnetic materials.

According to another embodiment, a guide tube assembly is provided. The guide tube assembly includes a guide tube configured to receive a catheter therethrough; and an inflatable member coupled to the guide tube, the inflatable member being slidably adjustable along the length of the guide tube, the inflatable member configured to expand radially inwardly and outwardly.

Any one of the above embodiments (or examples of those embodiments) may be provided alone or in combination with any one or more of the examples of that embodiment discussed above; e.g., the first embodiment may be provided alone or in combination with any one or more of the examples of the first embodiment discussed above; and the second embodiment may be provided alone or in combination with any one or more of the examples of the second embodiment or first embodiment discussed above; and so-forth.

Additional features and advantages will be set forth in the detailed description which follows, and in part will be readily apparent to those skilled in the art from that description or recognized by practicing the embodiments as described herein, including the detailed description which follows, the claims.

BRIEF DESCRIPTION OF THE DRAWINGS

The above and other features, examples and advantages of embodiments or examples of the present disclosure are better understood when the following detailed description is read with reference to the accompanying drawings.

FIG. 8A illustrates an inflatable mechanism for holding a guide tube in position in accordance with another embodiment.

FIG. 8B illustrates a cross-sectional view of FIG. 8A in accordance with an embodiment.

FIG. 12A illustrates an example guide tube assembly including inner and outer inflatable mechanisms in uninflated states in accordance with an embodiment.

FIG. 12B illustrates the guide tube assembly of FIG. 12A in which the inner and outer inflatable mechanisms are in inflated states in accordance with an embodiment.

FIG. 13 illustrates an example inflation system for a guide tube assembly in accordance with an embodiment.

FIGS. 16A and 16B illustrate a schematic view of an example access port in accordance with an embodiment.

FIG. 17 illustrates a section of a cranial diaphragm with an access port assembly installed in accordance with one embodiment.

DETAILED DESCRIPTION

Figure 1:
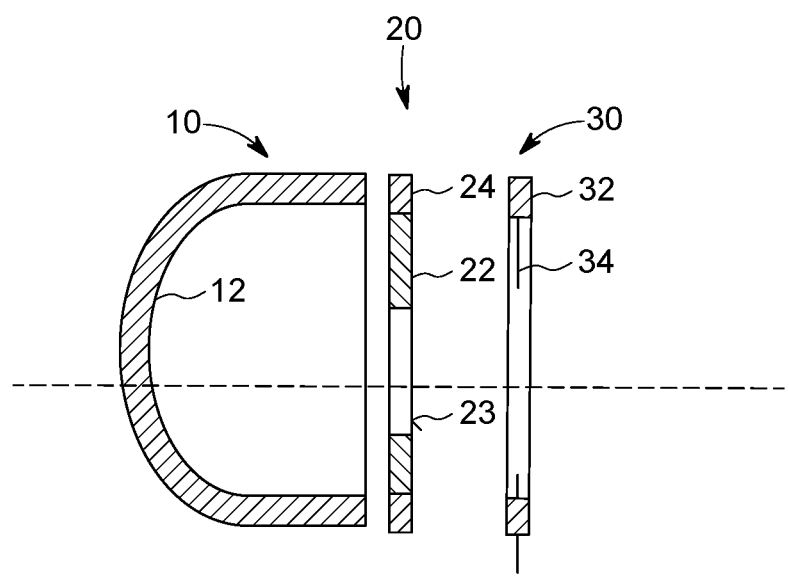
FIG. 1 illustrates a schematic, cross-sectional illustration of a conventional MRgFUS device.

Example embodiments are described and illustrated herein. These illustrated examples are not intended as limitations on the systems and methods described herein. For example, one or more aspects of the system can be utilized in other embodiments and other types of instruments. Such systems may, however, be embodied in many different forms and should not be construed as limited to the embodiments set forth herein. Like, but not necessarily the same, elements in the various figures are denoted by like reference numerals for consistency. Terms such as "first," "second," "front," "rear," "inner," and "outer" are used merely to distinguish one component (or part of a component or state of a component) from another. Such terms are not necessarily intended to denote a preference or a particular orientation.

Under most circumstances, extravascular blood that pools in the brain converts into a gel with maximum viscosity in several minutes. The viscosity is near enough to the surrounding brain viscosity that increasing the intensity of an aspiration catheter may pose local injury when small bore catheters are used. Additionally, negative pressure applied through a small tube is not able to overcome the shear stress of the blood clot in the acute phase. Hematoma evacuation therefore requires an open or mini-open approach for direct visualization to manipulate the clot for safe aspiration. Eventually the clot will liquefy and could be easily drained but the delay in treatment, assuming survival, elevates the risk. The delay may lead to irreversible injury if not decompressed promptly.

In the case of superficial (e.g. subdural) brain hematomas, treatment of a clotted hematoma is possible and widely practiced because the brain itself is not violated as the clot is 'extra-axial'. Open craniotomy is thus the standard of care. However, in case of deep-brain hematomas surgical excision may not be possible or may be associated with a higher likelihood or degree of morbidity as discussed above, depending on location.

The precision, accuracy and control of an MRgFUS device is within millimeters, which renders such device suitable to identify and triangulate a deep brain clotted hematoma, and to focus ultrasound radiation on the triangulated clot to liquefy the hematoma. Once liquefied, it is necessary to drain the liquefied material in order to effectively treat the hematoma to improve recovery by restoring the brain back to a normal configuration. One example of an MRgFUS device that can be used with the present system is the EXABLATE NEURO™ device provided by Insightec™ in Israel. This device is currently marketed for treating essential tremor and Parkinson's disease. The device is docked to an MRI machine and can deliver up to 1,024 ultrasound waves across the skull of a patient to precisely ablate a target deep in the brain.

Referring initially to FIG. 1, a schematic, cross-sectional illustration of a conventional MRgFUS device is depicted. The device includes a focused ultrasound transducer assembly 10, a cranial diaphragm 20 and a skull fixture 30. Briefly, the transducer assembly 10 comprises an array of ultrasonic transducers distributed over a substantially hemispherical frame and is configured to deliver ultrasonic energy to the cranium of a patient under treatment. By separately controlling the individual transducers within the array, a targeted and precisely controlled dose of ultrasonic waves can be delivered to a triangulated position within the patient's cranium. The cranial diaphragm 20 is composed of a diaphragm membrane 22 extending radially inward from a rigid circular frame 24. The diaphragm membrane 22 has an opening 23 at its center, which is cut and sized to elastically stretch over and provide a conformal circumferential seal against the patient's shaved scalp. The circular frame 24 is sealingly mated to the rim of the transducer assembly 10 (e.g. via an intermediate O-ring gasket) to provide a watertight seal therebetween. When positioned on a patient, the dome of the patient's head penetrates the hemispherical space defined within the transducer assembly 10. This space defines a jacket bounded by an interior surface 12 of the transducer assembly 10 and the cranial diaphragm 20 that caps its opening. The jacket is filled with chilled water or other fluid, which acts as a medium to conduct ultrasound waves between the transducer array on the transducer assembly 10 and the patient's head. The patient's head is held stationary via the skull fixture 30, which can include a series of fixturing pins 34 extending radially inward from a perimeter frame 32. The pins can be driven into the patient's skull via local anesthetic to ensure the head remains fixed during the procedure.

The MRgFUS device is configured to be docked to a conventional MRI machine so that ultrasound energy can be delivered to triangulated locations within the patient's brain identified via MRI image guidance. As noted, use of the conventional MRgFUS system is indicated for treatment of essential tremor and Parkinson's disease, where it is used to triangulate a discrete thalamic nucleus via MRI imaging followed by ultrasonically lesioning the brain at that location. MRI imaging is used throughout the procedure, intermittently with successive doses of ultrasound energy, to image and track a forming lesion and help guide successive ultrasound doses in order to achieve a lesion of desired geometry, location and size. While a frame is used to hold the head, the procedure does not use any incisions. The ultrasound waves are focused on the target through the transducers mounted in a helmet apparatus. The energy from the summation of the waves heats the tissue enough to denature the protein (typically >55 C). This selectively 'lesions' the brain. Disclosed here is a suite of tools that could be integrated with the existing MRgFUS device and used in real time to guide treatment.

Figure 2:
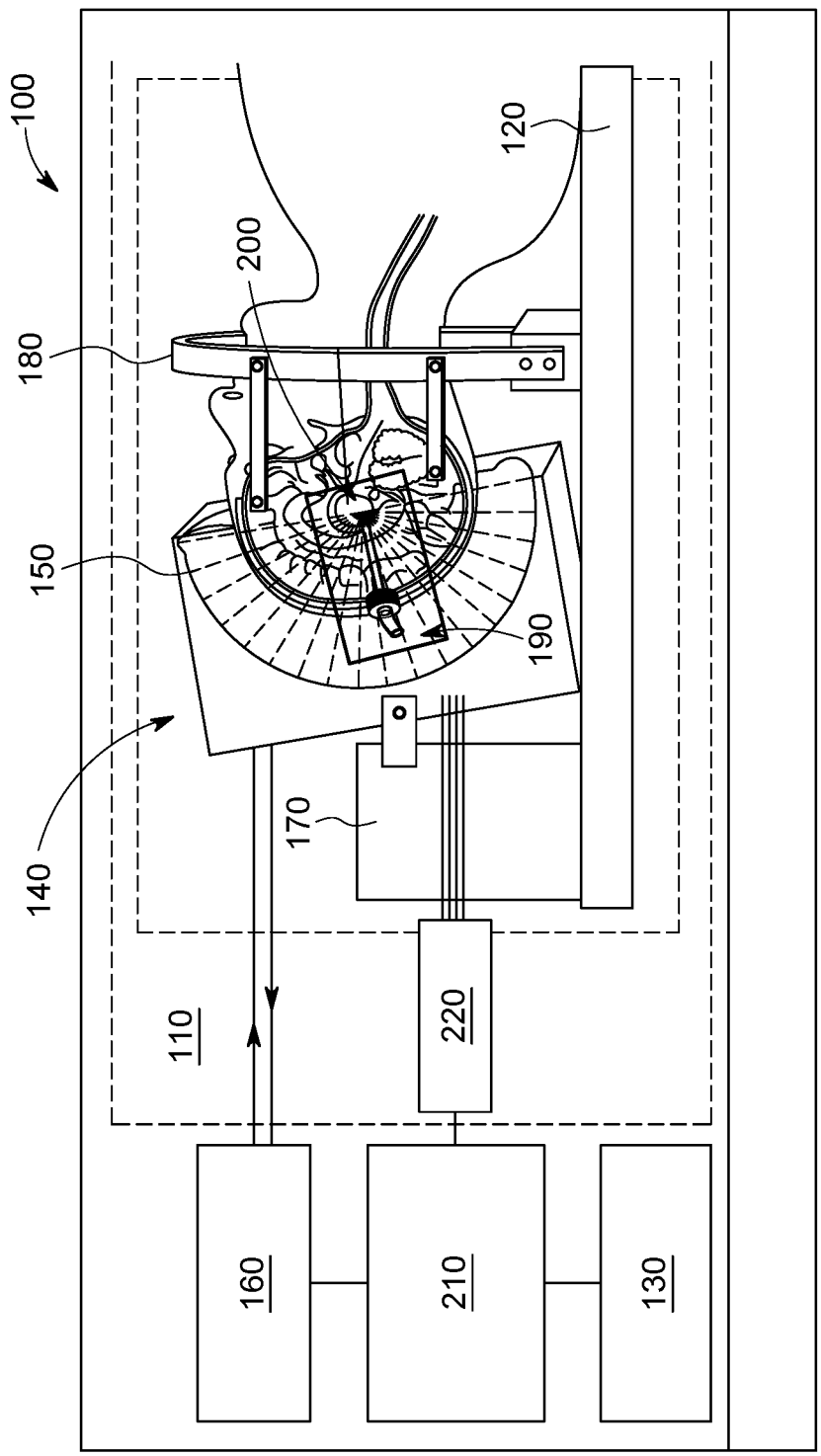
FIG. 2 illustrates a schematic diagram of a system for MRI-guided focused ultrasound aspiration in accordance with an embodiment.

Turning now to the present embodiment, a system and method are provided in which a body within the brain (or other organ) can be located and accessed for treatment. An MRgFUS device can be used not to lesion thalamic nuclei, but rather to triangulate and liquefy thrombotic material deep within the brain. The liquified material then can be suction aspirated via an emplaced catheter. FIG. 2 illustrates a system 100 for magnetic resonance-guided focused ultrasound aspiration in accordance with an example embodiment. The system 100 includes a conventional MRI environment 110, which generally comprises a bed or patient support 120, an MRI scanner, and an MRI workstation 130. The MRI environment 110 can be provided as an MRI suite having a control room for the MRI workstation 130 and a separate magnet room that houses the MRI scanner, or any other suitable environment. An MRgFUS device is provided which comprises a transducer assembly 140 coupled to a cranial diaphragm 150. The transducer assembly 140 includes a plurality of transducers arranged in an array and mounted in a helmet apparatus or in a substantially hemispherical manner and configured to surround a portion of a patient's head. The cranial diaphragm 150 is configured to surround another portion of the patient's head and comprises a membrane that can function as a cooling system. For instance, the membrane can be configured to retain a liquid therein, such as degassed water, which is coupled to a liquid circulation, cooling, and degassing system 160 so that an appropriate and comfortable temperature of the patient's head can be maintained during treatment. A mechanical positioning system 170 can also be provided to suitably position the transducer assembly 140 with respect to the patient and the MRI scanner. A stereotactic frame 180 can be secured to the patient's head to provide reference points for targeting and to hold the head secure during treatment, thereby preventing unwanted motion.

A device 190 for access to and treatment of a deep-seated body 200, such as a blood clot, or tumor is provided, which will be described in greater detail below. A focused ultrasound workstation 210 includes a processor configured for treatment planning, thermometry, and dosimetry and is in communication with a driving system 220. The driving system 220 receives signals from the processor and in turn, directs the transducer assembly 140 to generate ultrasound energy. The MRI scanner is used to guide the application of ultrasound energy to the body 200.

Figure 3:
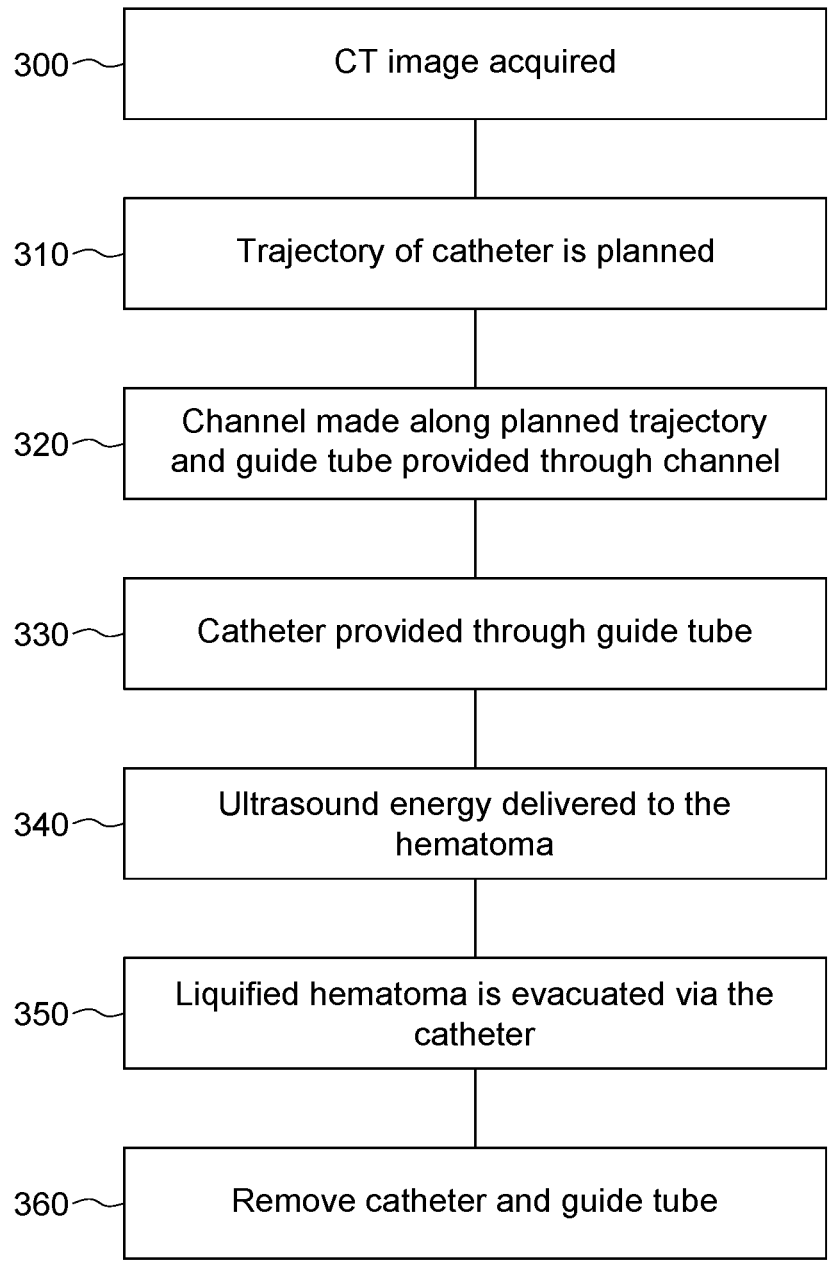
FIG. 3 illustrates a method for aspiration of a hematoma using magnetic resonance-guided focused ultrasound in accordance with an embodiment.
Figure 4:
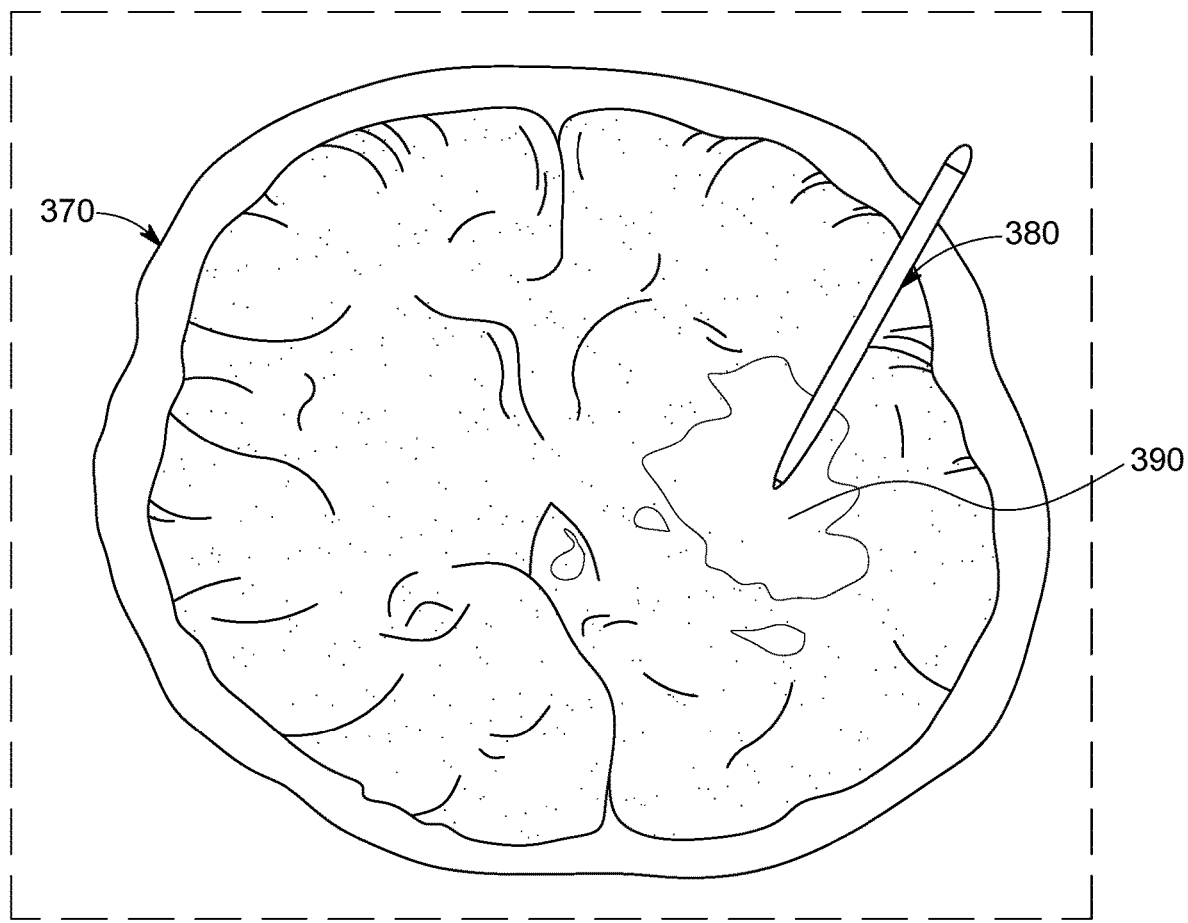
FIG. 4 illustrates an example of a CT image of a brain showing a hematoma.

FIG. 3 illustrates an example method for aspirating and/or treating a body that employs magnetic resonance-guided focused ultrasound. The body is described herein as a hematoma or blood clot; however, it is to be appreciated that any other suitable body, such as a tumor, can be treated with the described system and method. To carry out this procedure, a catheter or tool is placed at the body, and the surgeon is given cranial access to reposition the device based on image guidance during the procedure. Accordingly, at the start of the example method, an image of the hematoma is acquired. For instance, at 300, stereotactic computed tomography (CT) is used to precisely locate the hematoma within the brain. Alternatively, magnetic resonance imaging (MRI) can be used to image the hematoma. Once the hematoma is located, a trajectory for a catheter is planned to minimize tissue injury and maximize clot evacuation at 310. FIG. 4 illustrates an example of a CT image 370 with a planned trajectory for placement of a device 380 used to access the hematoma 390. At 320, a channel is defined along the planned trajectory to provide communication from an opening in the skull to the hematoma. The channel can be defined by the insertion of a thin guide tube, which is configured to accommodate one or more catheters or other tools therethrough for treatment of the hematoma.

Figure 5A:
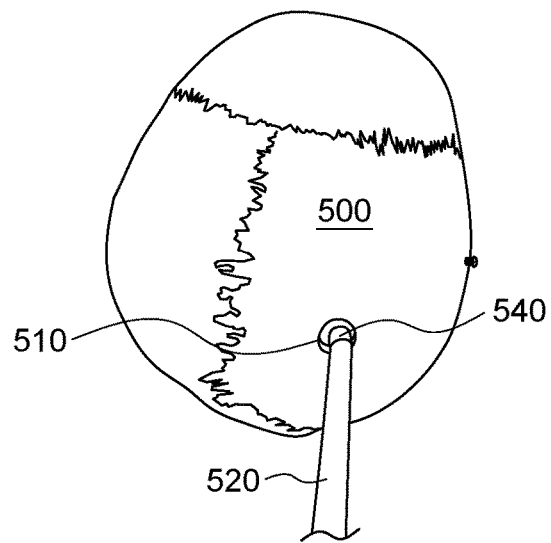
FIGS. 5A-5C illustrates an example of a guide tube inserted and held in position in accordance with an embodiment.
Figure 5B:
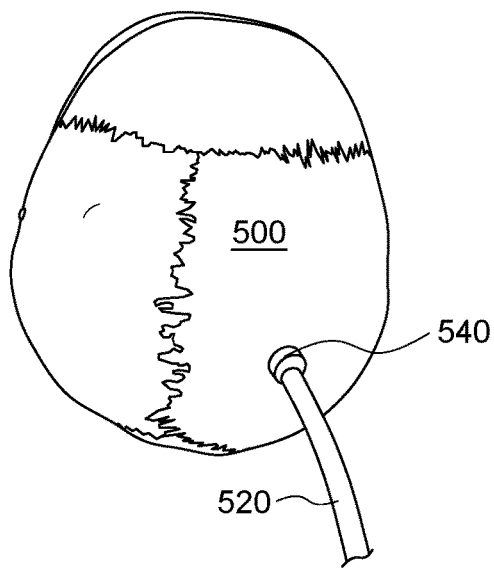
Figure 5C:
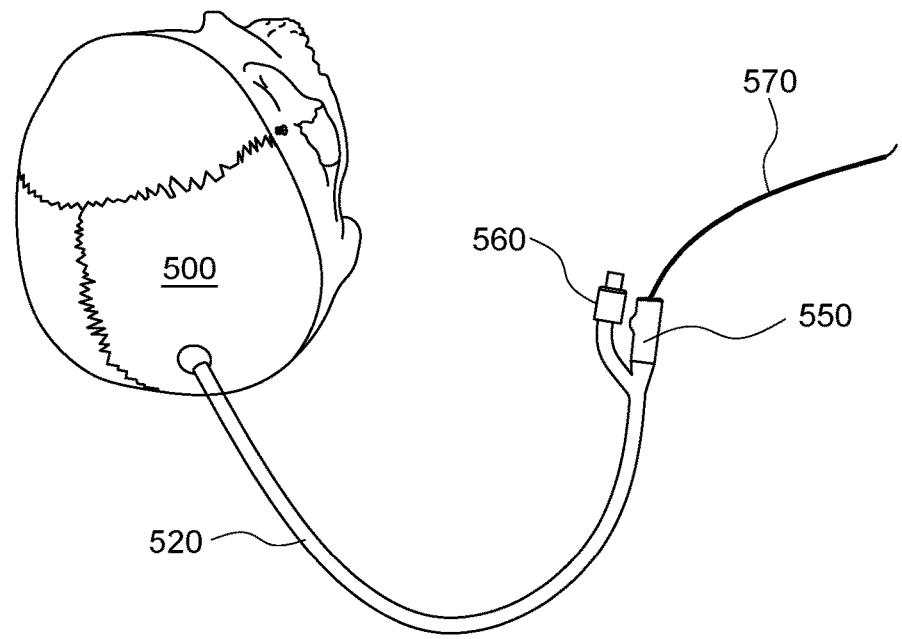

An example of how a guide tube can be inserted is illustrated in FIGS. 5A through 5C. A small incision is first made in the patient's scalp to define an entry point. Then, as shown in FIG. 5A, an opening 510 is made in the skull 500. A guide tube 520 is then inserted through the skull 500 and guided into an appropriate position, such as until a distal end of the guide tube 520 is disposed proximate or within the hematoma. Localization imaging such as a CT scan can be used to stereotactically insert the guide tube 520 using commercially available navigation software and hardware such those available from BrainLab™ or Medtronic™. Alternatively, MRI can be used to position the guide tube 520 into place. It is to be appreciated that the guide tube 520 could be initially inserted more superficially and then advanced as necessary. A portion of the guide tube 520, where it emerges from the skull, could be secured to the bone. Alternatively, the guide tube can include a balloon portion 540 used to hold the guide tube 520 in place relative to the skull. The balloon portion 540 can be formed as a materially integral component of the guide tube 520. With this configuration, the guide tube 520 is inserted into skull until the balloon portion 540 is aligned with the opening 510 in the skull 500, as shown. The balloon portion 540 is then inflated to hold the assembly in place using the skull 500 as a support (FIG. 5B). The guide tube 520 can include a first end port 550 through which one or more instruments 570 used to remove the clot and/or administer agents are passed through the guide tube 520. The guide tube 520 can also include a second end port 560 used for inflating and deflating the balloon portion 540.

Turning back to FIG. 3, once the guide tube has been placed, the patient's head is immobilized and positioned within the MRgFUS device, as illustrated in FIG. 2. At 330, an aspiration catheter can be provided through the guide tube such that a distal end of the catheter is positioned within the hematoma. Then, at 340, ultrasound energy is delivered via MRI image guidance to the hematoma. The ultrasonic energy can be directed and focused on the hematoma to liquefy it without damaging the tissue around it. Once liquified, the hematoma is evacuated via the catheter at 350. During evacuation, the distal end of the catheter may need to be repositioned as the shape of the hematoma changes. Real-time MRI imaging can be used to guide this repositioning of the catheter. By ensuring that the distal end remains or is repositioned at the base of pooling liquid, the hematoma can be entirely or substantially removed. Image guidance also can be used to refocus delivery of the ultrasound energy in conformity with the evolution of the hematoma as it is sonicated and evacuated, to ensure it is fully liquefied for removal. Once the hematoma has been partially or fully removed, which can be verified via MRI, the patient can be removed from the MRgFUS system and the catheter and guide tube withdrawn (360). If a balloon was used to secure the guide tube, once the aforementioned procedure is complete, the balloon is deflated and the guide tube can be removed from the patient without opening up the skin again, as will be described in more detail below.

The guide tube, catheter, and any other tools or instruments used with the MRgFUS system are of relatively small diameter and made of a non-ferromagnetic material, such as plastic or a silicone-based material. By using a suitable non-ferromagnetic material, none of the guide tube, catheter, or other tools will be moved by the magnetic fields, induce unwanted heating, or cause confounding imaging artifacts during the procedure. The small diameter renders the guide tube substantially insignificant within the jacket defined at the interior of the transducer assembly. The guide tube may emerge from the patient's scalp at a position within the jacket. The guide tube can be 7 gauge or smaller, and more preferably 14 gauge or smaller. At least one catheter and/or tool that is advanced through the guide tube has a diameter that is smaller than the diameter of the guide tube and where appropriate, up to 34 gauge. To access the guide tube with the catheter and/or tool, the guide tube penetrates the MRgFUS device to reach the external environment via an access port, as described further below. The catheter or other surgical implement to treat and/or drain clot material or other target can be inserted from the external environment via the guide tube and manipulated and/or repositioned by a surgeon for treatment. A proximal end of the catheter can extend beyond a proximal end of the guide tube. In the case of aspirating a hematoma, a suction apparatus can be coupled to the proximal end of the catheter. The suction may be manual or automated. A negative pressure setting for the suction apparatus can be adjustable.

Figure 6:
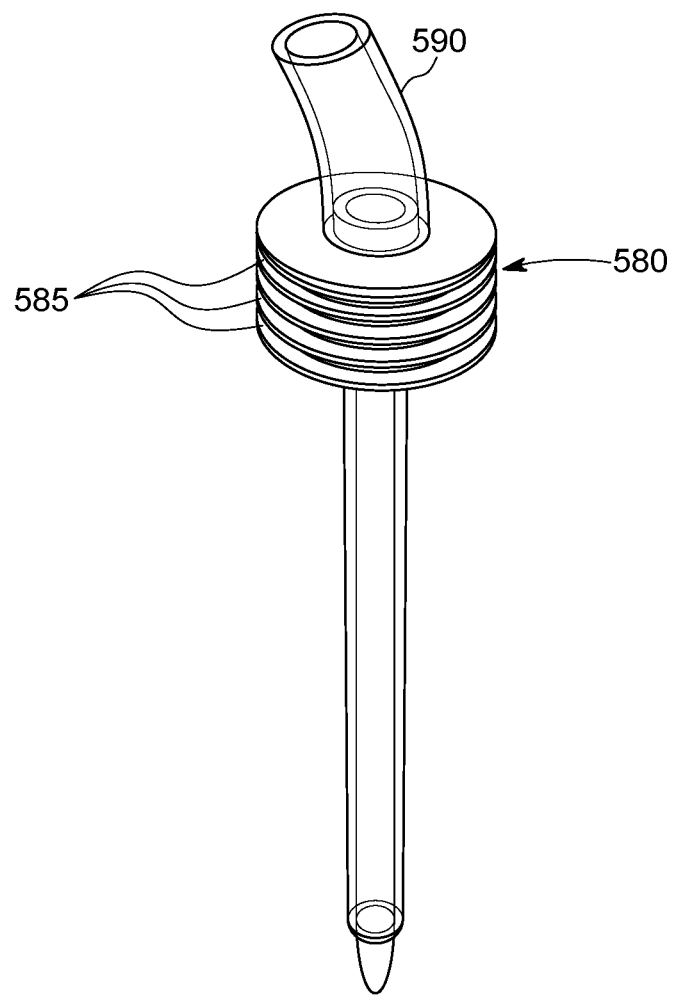
FIG. 6 illustrates a screw mechanism for holding a guide tube in position in accordance with an embodiment.

FIG. 6 illustrates an example of another mechanism for holding a guide tube in position in the skull of a patient. The mechanism includes a cylindrical insert 580 having an outer diameter that corresponds with an opening (such as opening 510) made in the skull. The outer diameter is provided with threads 585 that allow the insert 580 to be threaded and securely positioned in place in the bone. An inner diameter of the insert 580 corresponds with an outer diameter of a guide tube 590 such that the guide tube 590 is securely held by the insert 580. The guide tube 590 can be a one-piece tube that fits through the inner diameter of the insert 580, or it may include a top tube portion and a separate bottom tube portion, each of which can be secured within the insert, such as through threaded connections.

Figure 7:
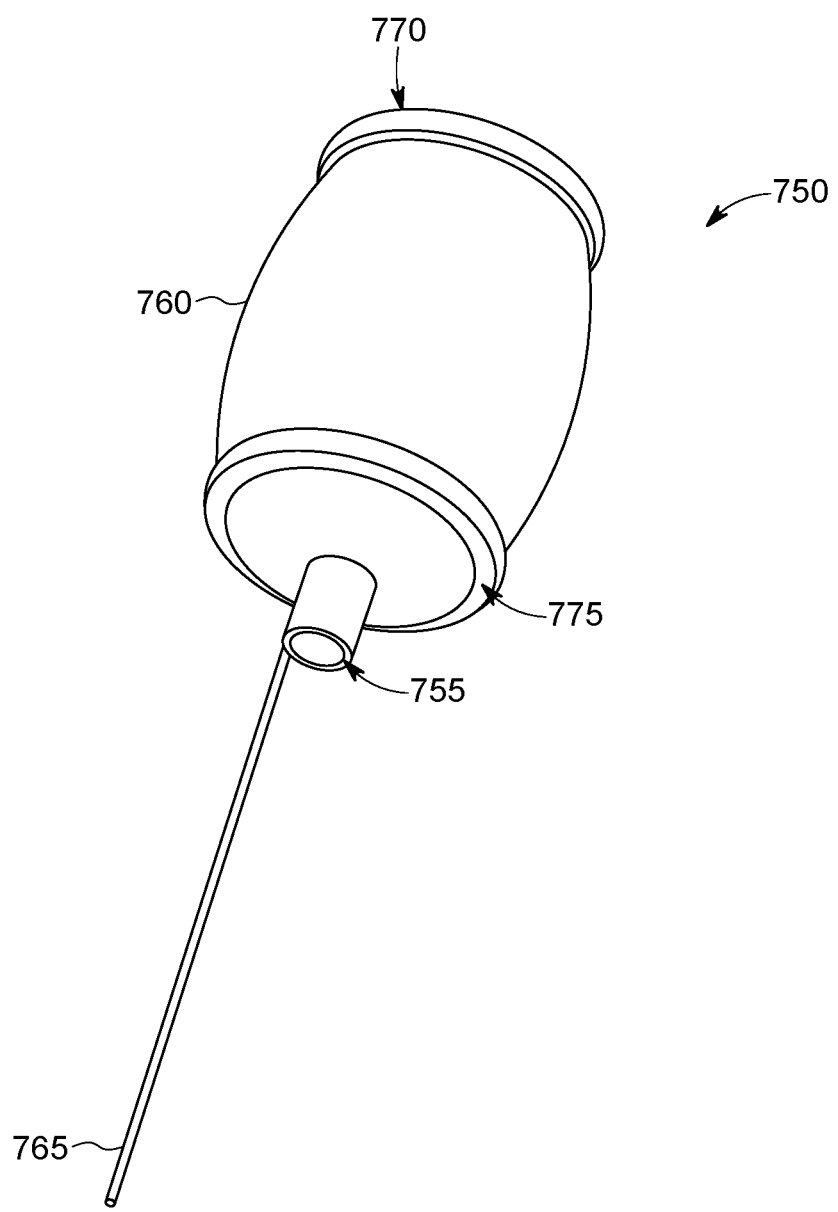
FIG. 7 illustrates an inflatable mechanism for holding a guide tube in position in accordance with an embodiment.

FIG. 7 illustrates an example of an inflatable member 750 or balloon that can be used to hold a guide tube in position within the skull. The inflatable member 750 includes a substantially flexible inner surface (not shown), which defines an opening 755 therethrough for insertion of the guide tube. The outer wall 760 of the insert is also made of a flexible material and a space between the inner and outer walls is confined but for a small sealable opening. Thus, upon receiving an air or gas in the space, both the inner and outer walls of the insert can expand radially, thereby inflating the inflatable member 750. In its non-expanded or uninflated state, the outer diameter of the inflatable member 750 is smaller than an opening provided in the skull such that the inflatable member 750 can be placed within the opening. Once positioned, a liquid, such as saline, or a pressurized air or gas is provided through a thin communication tube 765 and into the insert space to expand the outer walls of the inflatable member 750 against the opening, thereby securing the inflatable member 750 in place. As the inner wall also expands, a guide tube positioned through the opening 755 will also be securely held in place when the inflatable member 750 is inflated. When secured within the opening, a first end cap 770 is positioned at an inside surface of the skull bone and a second end cap 775 is positioned at an outside surface of the skull, which mitigates the inflatable member 750 from being pushed or pulled out of the skull opening. While the inflatable member 750 can secured against an opening in the skull similar to the balloon portion 540 described with respect to FIGS. 5A-5C, because the inflatable member 750 is not materially integral with the guide tube as in FIGS. 5A-5C, the inflatable member 750 can be moved longitudinally along the guide tube, which facilitates adjustability and placement of the distal end of the guide tube proximate the body to be treated.

Figure 9B:
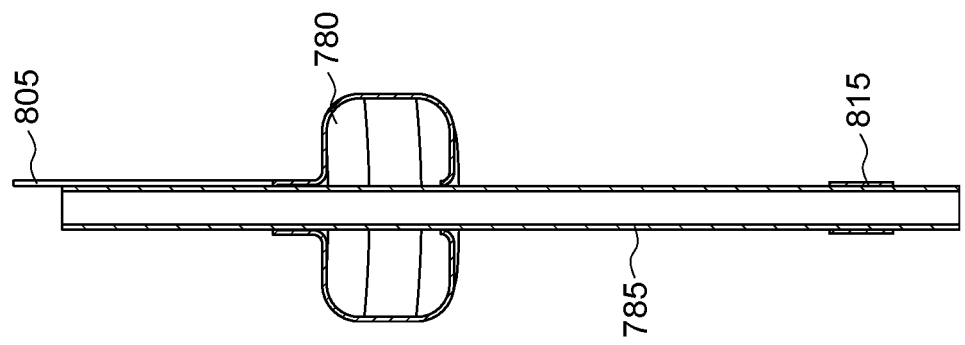
FIG. 9B illustrates a cross-sectional view of FIG. 9A in accordance with an embodiment.
Figure 9A:
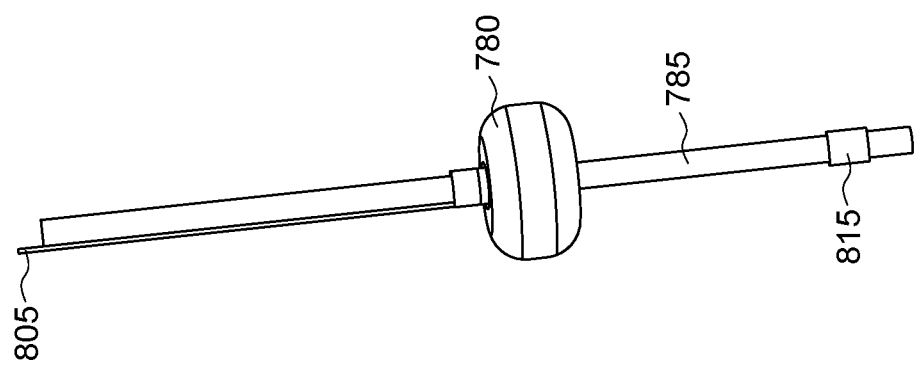
FIG. 9A illustrates the inflatable mechanism of FIG. 8A provided on a guide tube in accordance with an embodiment.

FIGS. 8A and 8B illustrate another example of an inflatable member 780 or balloon that can be used to hold a guide tube in position within the skull. FIGS. 9A and 9B illustrate the inflatable member 780 slidably engaged with a guide tube 785 in accordance with an embodiment. The inflatable member 780 comprises a substantially torus-shaped body. An outer diameter of the body is sized to correspond with an opening made within a skull. An inner diameter of the body corresponds with an outer diameter of the guide tube 785. Thus, the guide tube 785 is sized to fit through a central opening 790 in the inflatable member 780. A collar 795 can extend upwardly from the torus-shaped body and provides an interference fit between an inner diameter of the collar 795 and an outer diameter of the guide tube 785. The collar 795 includes a sealable opening in communication with an inner portion of the body to facilitate inflation and deflation thereof. A communication channel 805 is secured within the opening in the collar 795 through which a gas and/or liquid can travel to provide the inflation and deflation of the inflatable member 780. The communication channel 805 extends alongside an outer surface of the guide tube 785 and can be coupled thereto. When in a deflated state, the fit between the inflatable member 780 and the guide tube 785 is tight but still allows for movement or adjustability of the inflatable member 780 along the length of the guide tube 785.

Similar to the method described above, to place the guide tube 785, an incision is first made in a patient's scalp and then an opening is made in the skull. The guide tube 785 can then be placed along the planned trajectory until a distal end is positioned proximate a target body to be treated. The inflatable member 780 can then be slidably moved along a length of the guide tube 785 until the inflatable member 780 is positioned within the skull opening. Alternatively, the inflatable member 780 can be pre-positioned at a distance from the distal end of the guide tube 785, as determined during the trajectory planning stage, and held in place via the interference fit between the collar 795 and the guide tube 785. Once in place, the member 780 is inflated via the communication channel 805. The torus-shaped body allows for inflation at both the inner and outer diameter of the inflatable member 780 thereby securing the member 780 in place against both the guide tube 785 and the skull, which in turn, secures the guide tube 785 in position with respect to the skull. The incision made in the patient's scalp is closed and the guide tube 785 and communication channel 805 can then be tunneled beneath the scalp to exit the scalp at a position away from the incision site. During removal of the guide tube 785, the inflatable member 780 is deflated via the communication channel 805 and the entire guide tube 785 and inflatable member 780 assembly can be pulled from the skull without reopening the initial incision site. A stopper 815 can be secured to or materially integral near a distal end of the guide tube 785. The stopper 815 has an outer diameter that is larger than the central opening 790 of the inflatable member 780. Thus, the stopper 815 mitigates separation, of sliding off, of the inflatable member 780 from the guide tube 785 during removal of the assembly from the patient.

The inflatable member 780, and the other inflatable members described herein, can be made from a semi-compliant and/or compliant yet puncture resistant material. For example, the body can include a polyurethane material coated with silicone. It is to be appreciated that any other suitable material can be used that allows inflation of the body to securely hold the inflatable member 780 against the skull opening while being puncture resistant against any sharp edges of the skull bone. The guide tube 785 can also be made from a flexible polymer material, such as silicone, to allow for sharp bends, such as 90-degrees, during tunneling.

Figure 10:
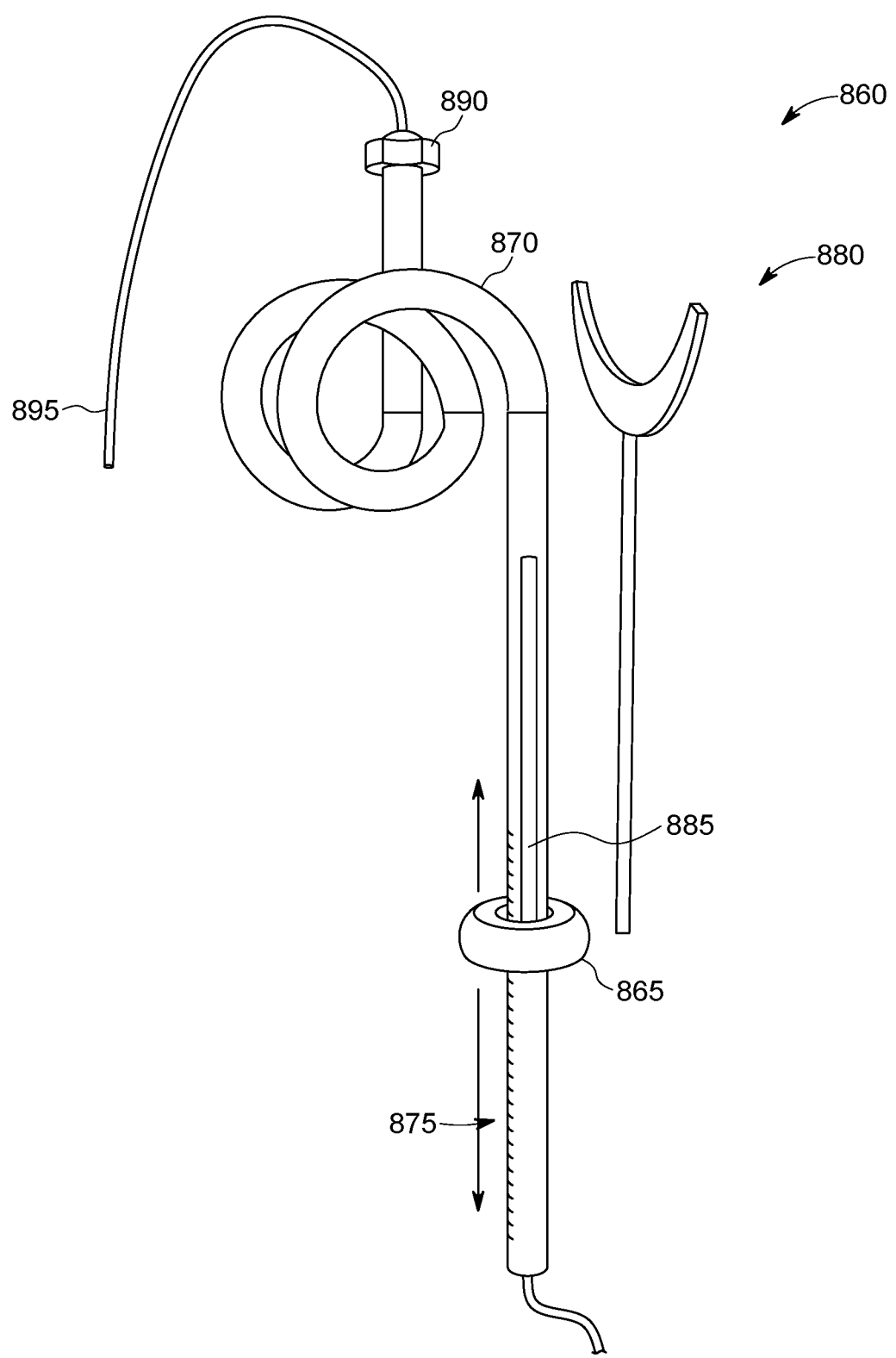
FIG. 10 illustrates an example guide tube assembly in accordance with an embodiment.

FIG. 10 illustrates an example guide tube assembly 860 having an adjustable balloon component or inflatable member 865, as described above. The balloon component 865 is provided around a guide tube 870 and adjusted to a desired location along the guide tube 870 based on a depth of a clot or body to be treated. For instance, the guide tube 870 is generally positioned such that the distal end is proximate a top portion of the clot. Thus, the distance between the top portion of the clot and the skull along the planned trajectory corresponds to a distance between the desired location of the balloon 865 and the distal end of the guide tube 870. A numbered depth gauge 875 can be provided on the tube to facilitate positioning of the balloon 865.

Figure 11:
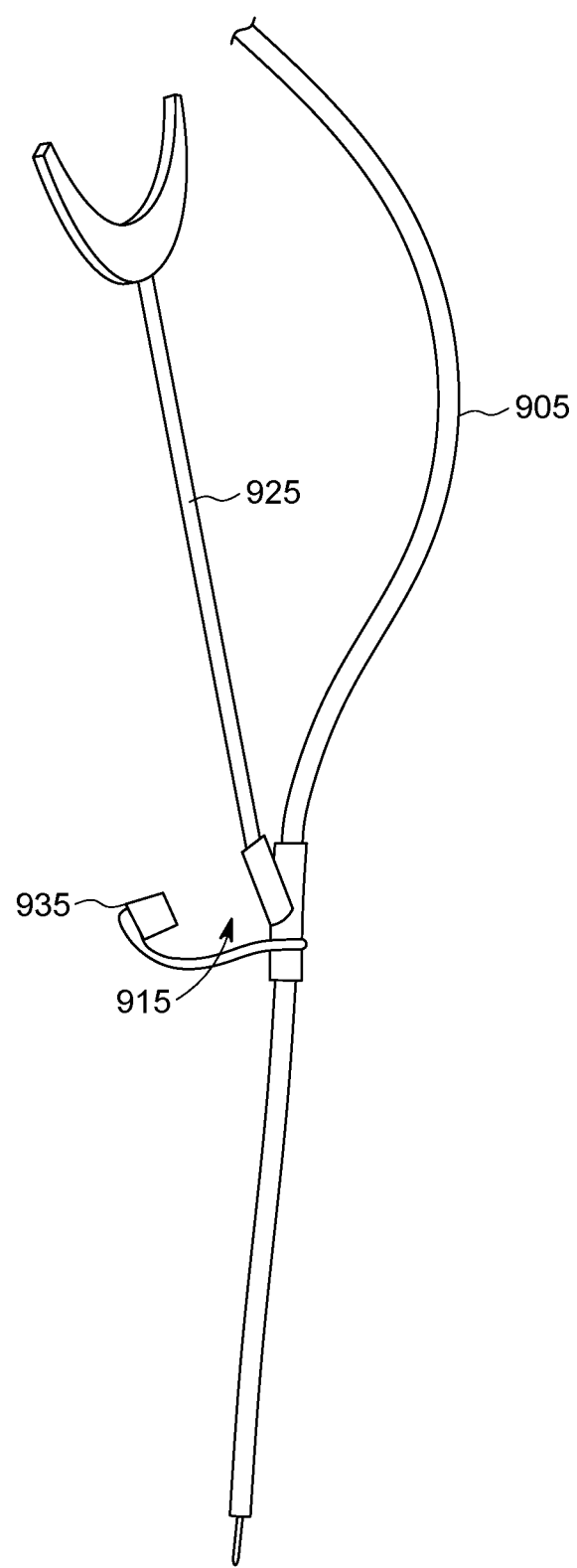
FIG. 11 illustrates an example guide tube assembly in accordance with an embodiment.

Because the guide tube 870 is made of flexible materials to accommodate sharp turns, the guide tube 870 may be too flexible to push through to the target location. Thus, the guide tube assembly 860 can also include a navigation tool, such as a stylet, 880 to assist in navigation of the guide tube 870 during placement. Because the navigation tool 880 is only needed temporarily, it can be positioned through a tube or channel 885 secured to a side of the guide tube 870, thereby simplifying insertion and removal of the navigation tool 880. It is also not necessary for the stylet to be made from an MRI-compatible material and thus, can be made from a stainless steel or other stiff wire material. The navigation tool 880 can be a Medtronic or Brainlab stylet, or any other suitable tool to facilitate accurate guidance and placement of the guide tube 870 proximate the clot. FIG. 11 illustrates an example of a guide tube 905 configured with a low-profile secondary channel, such as a Y-channel, 915 that can branch off the guide tube 905. This secondary channel 915 allows for insertion of a navigation tool 925 through the guide tube 905 and to its distal end. A cap 935 can be tethered to the secondary channel 915 to close off the channel when not in use. A Luer lock mechanism or other suitable mechanism can also be provided at an opening of the secondary channel 915 to allow for easy and secure insertion and removal of the navigation tool 925. After insertion, a dial lock, such as a Tuohy Borst adapter, can be provided to secure the navigation tool 925 in place during use. Once the guide tube 905 is positioned, the navigation tool 925 is removed.

Turning back to FIG. 10, at a proximal end of the guide tube 870, a dial lock mechanism 890, such as a Tuohy Borst adapter, is provided. Once the guide tube 870 has been placed and the patient is moved to and positioned within the MRgFUS system, a catheter 895 can be threaded through the guide tube 870. In the case of aspirating a blood clot, the catheter 895 is positioned such that its distal end extends past the distal end of the guide tube 870 and into the clot. Once in position, the dial lock mechanism 890 is used to secure the catheter 895. The catheter 895 is configured to bend around sharp turns, such as a 90-degree angle at the skull entrance, be suitable kink resistant, and of a material that is MM-compatible. One example is a plastic coil reinforced tube suitable for aspirating a liquified body. Various other tools and catheters can be provided through the guide tube 870 for treatment of a target body.

FIGS. 12A, 12B, and 13 illustrate another mechanism of securing a guide tube assembly in accordance with an embodiment. A first balloon component 1020 can be secured to an outer wall of a guide tube 1025 and a second balloon component 1030 can be secured to an inner wall of the guide tube 1025. FIG. 12A illustrates the first and second balloon components 1020, 1030 in deflated states. When in the deflated states, the guide tube 1025 is inserted into an opening 1035 made in the skull 1040. Once aligned, the first balloon component 1020 can be inflated such that the first balloon component 1020 can anchor the guide tube 1025 to the skull bone 1040 (FIG. 12B). Once a catheter 1045, or other instrument, is inserted through the guide tube 1025, the second balloon component 1030 can be inflated to hold the catheter 1045 in position. It is to be appreciated that the dial lock mechanism 890 described in FIG. 10 can be used in place of the second balloon component 1030, if desired. Locking the catheter 1045, or other instrument, in place prevents migration during the procedure. As shown in FIG. 13, first and second inflation/deflation tubes 1050, 1060 can be provided to facilitate inflation and deflation of the first and second balloon components 1020, 1030, respectively. For instance, saline/air can be injected into or suctioned from the inflation tubes 1050, 1055 via syringes positioned outside of the MRgFUS device.

Figure 14:
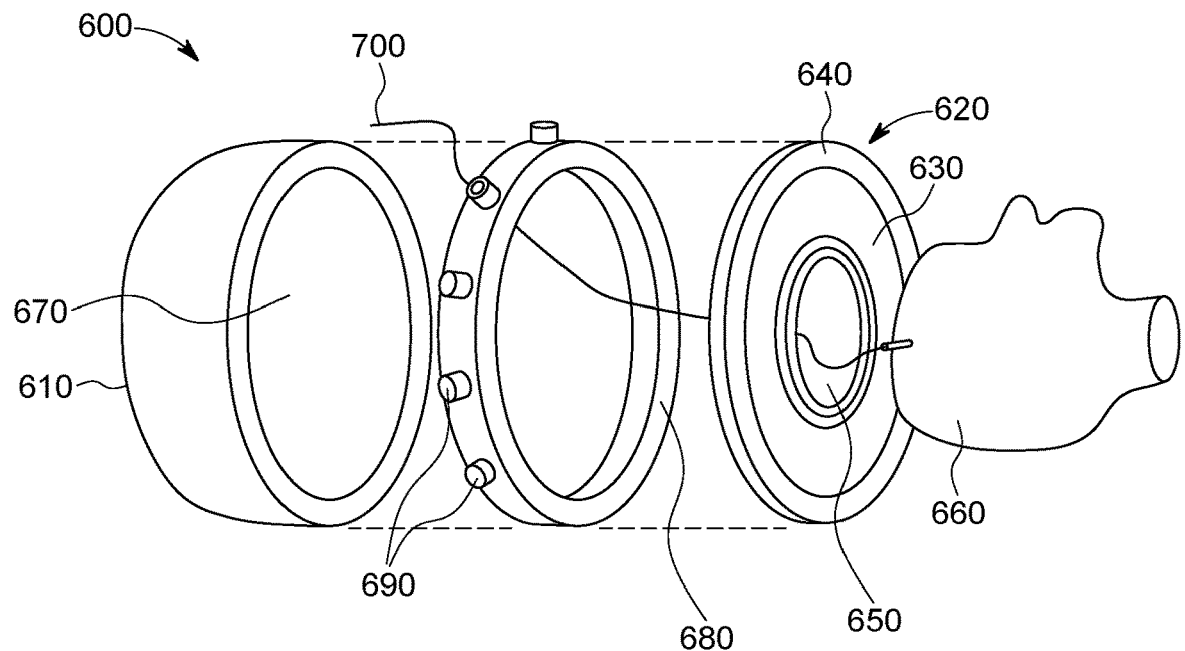
FIG. 14 illustrates a schematic view of an example MRgFUS device in accordance with an embodiment.

FIG. 14 illustrates an example MRgFUS device 600 that can be used with the systems and methods described herein. The MRgFUS device 600 includes a focused ultrasound transducer assembly 610 having an array of ultrasonic transducers distributed over a substantially hemispherical frame. For instance, the transducer assembly 610 can include an array of 1024 individual ultrasound transmitting elements. The individual elements can be controlled separately, thereby providing a targeted and precisely controlled dose of ultrasonic waves that can be delivered to a triangulated position within the patient's cranium. The MRgFUS device 600 also includes a cranial diaphragm 620, which includes a diaphragm membrane 630 extending radially inward from a rigid circular frame 640. The diaphragm membrane 630 has an opening 650 at its center. The opening 650 is sized to elastically stretch over and provide a conformal circumferential seal against the patient's scalp 660. The circular frame 640 is sealingly mated to the rim of the transducer assembly 610, such as via an intermediate O-ring gasket (not shown), to provide a watertight seal therebetween. When positioned on a patient, the dome of the patient's head penetrates the hemispherical space defined within the transducer assembly 610. This space defines a jacket 670 bounded by an interior surface of the transducer assembly 610 and the cranial diaphragm 620 that caps its opening. The jacket 670 is filled with chilled water or other fluid, which acts as a medium to conduct ultrasound waves between the transducer array on the transducer assembly 610 and the patient's head 660.

An access ring 680 can be interposed between the transducer assembly 610 and the cranial diaphragm 620. The access ring 680 includes a substantially circular frame having one or a plurality of access ports 690 distributed about its circumference. The access ports 690 are configured to provide access from the external environment into the MRgFUS device 600 through the access ring 680. The frame of the access ring 680 can be secured between the transducer assembly 610 and the frame 640 of the cranial diaphragm 620 using any suitable fastener while maintaining a substantially water-tight seal within the jacket 670. For example, the access ring 680 can be fitted with complementary hardware and structure at a first side so that the cranial diaphragm 620 will mate with and be secured thereto in the same manner as it otherwise would mate to the transducer assembly 610. Likewise, the access ring 680 can be fitted with complementary hardware and structure at a second, opposing side so that the transducer assembly 610 will mate and be secured thereto in the same manner as it otherwise would mate to the cranial diaphragm 620. Thus, the access ring 680 becomes integrated with the MRgFUS device 600 to help define the water-tight jacket 670 that holds circulating ultrasound medium (preferably chilled water) when used in the disclosed methods to aspirate liquefied thrombotic material. A first seal can be provided between an end surface of the transducer assembly 610 and the second side of the access ring 680 and a second seal can be provided between the first side of the access ring 680 and a corresponding side of the frame 640 of the cranial diaphragm 620 to provide a watertight structure. The first and second seals can be O-ring gaskets or any other suitable gasket. Alternatively, or additionally, machined mating surfaces opposing one another may be compressed together to form the first and second seals.

Procedurally, a guide tube 700 is first placed in the patient's cranium 660 as described above. The guide tube 700 is then threaded through an available access port 690 in the access ring 680 so that a proximal end of the guide tube 700 emerges from the access ring 680 to the exterior environment. Then, the patient is fitted within the MRgFUS device 600 with its head conformally and water-tightly received through the opening 650 at the center of the diaphragm membrane 630, and within the jacket 670 defined at the center of the transducer assembly 610. With the access ring 680 in-place and secured to the both the transducer assembly 610 and the cranial diaphragm 620 as described, the ultrasound medium (e.g., chilled water) can be filled and circulated through the jacket 670 to complete the assembly prior to an MM-guided ultrasound treatment to liquefy a target body, such as a hematoma, deliver a therapeutic agent, and/or treat the target body via one or more other tools. Ideally, any slack is removed from the guide tube 700 within the assembled MRgFUS device 600, such as during assembly, so that the guide tube 700 remains unbunched within the jacket 670 between the scalp 660 and the transducer assembly 610, on its way to the access port 690 where it exits the assembled MRgFUS device 600. Alternatively, the guide tube 700 may be tunneled beneath the scalp a short distance and then perforate the scalp to minimize interference with the transducer ultrasound waves. The guide tube 700 may also need to be affixed via adhesives or anchors resting on top of the scalp.

The access ports 690 can be provided with self-healing silicone diaphragms to ensure maintenance of a water-tight seal at each of the ports 690. For example, the self-healing diaphragms can be needle-punctured to provide a passage through which the guide tube 700 may be threaded. Once threaded, the diaphragm will compress (i.e. 'heal') radially inward against the guide tube 700 passing therethrough, essentially closing the diaphragm (and the associated port 690) about the guide tube 700.

Figure 15:
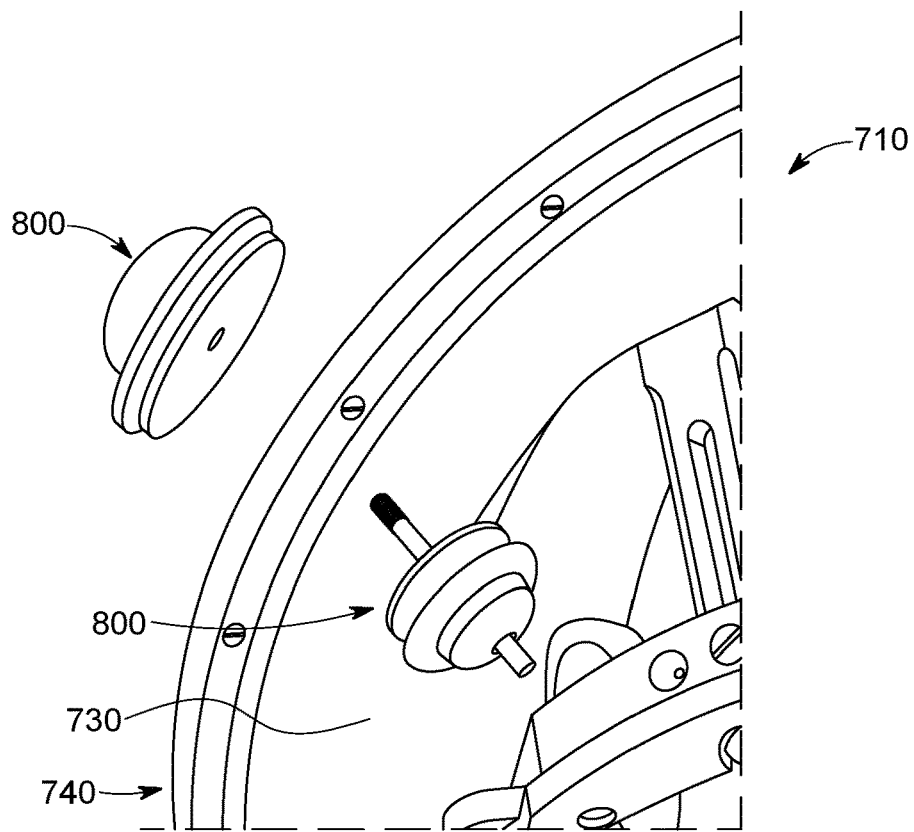
FIG. 15 illustrates a section of a cranial diaphragm and access port assembly in accordance with another embodiment.

FIG. 15 illustrates a portion of an MRgFUS device 710 in accordance with another example embodiment. In this embodiment, the MRgFUS device 710 includes a hemispherical transducer assembly and a cranial diaphragm, as described above. However, rather than an access ring positioned between the transducer assembly and the cranial diaphragm, access ports 800 are provided directly in the diaphragm membrane 730 of the cranial diaphragm 740. The diaphragm membrane 730 includes one or more discrete access ports 800 disposed therein, preferably a plurality of access ports distributed about a circular path around the diaphragm membrane 730. As with the aforementioned access ring 680, distributing the access ports 800 around the diaphragm membrane 730 provides access at a multitude of different locations. This helps avoid the need to ensure a specific angular alignment of the cranial diaphragm 740 (or of the access ring 680 in the earlier embodiment) so that an access port 800 will be positioned in a desired location. It also can be desirable if multiple access ports are useful or necessary for a single procedure. Tunneling the guide tube beneath the scalp or anchoring on the surface may be needed with this approach. By tunneling the guide tube, the opening in the scalp can be moved to an area outside the chilled water bath. This configuration is also beneficial to mitigate contamination of the water with blood and/or potential contamination with instruments provided through the guide tube.

FIGS. 16A and 16B illustrate an example access port 800 that can be secured directly to the diaphragm membrane 730. The access port 800 includes a first body portion 810 and a first gasket 820 and an opposing second body portion 830 and a second gasket 840. The first body portion 810 includes a substantially planar surface that is secured to a first surface of the first gasket 820. Similarly, the second body portion 830 includes a substantially planar surface that is secured to a first surface of the second gasket 840. The first and second body portions 810, 830 include an aperture sized to receive a cylindrical sleeve 850 therethrough. The cylindrical sleeve 850 is sized to receive a guide tube and/or at least one catheter or instrument therethrough. The cylindrical sleeve 850 is optional and alternatively, the guide tube can extend directly through the aperture provided in the access port 800.

As shown in FIG. 17, when coupling the access port 800 to the diaphragm membrane 730, a second surface of the first gasket 820 is secured to an outer surface (a side facing the external environment, or the surgeon) of the diaphragm membrane 730. Then, the sleeve 850, which can have the second body portion 830 and second gasket 840 positioned thereon, is pushed through an aperture or small perforation in the diaphragm membrane 730 and through the first gasket and aperture in the first body portion 810. A second surface of the second gasket 840 is then secured to an inner surface (a side facing the patient) of the diaphragm membrane 730. Each of the first and second gaskets 820, 840 are configured to seal against the diaphragm membrane in a liquid-tight manner. For instance, the first and second gaskets 820, 840 can be formed or provided with self-healing portions through which the sleeve 850 is pushed. If not positioned during assembly of the access port 800 body to the diaphragm membrane 730, the sleeve 850 may be fed from an inner portion of the MRgFUS device through the second body portion 830 and second gasket 840, through the diaphragm membrane, and then through the first gasket 820 and first body portion 810 to the external environment. The first and gaskets 820, 840 provide the required liquid-tight seal so that the diaphragm membrane 730 can hold a cooling agent, such as water, while permitting a guide tube, catheter, lead, or the like to pass through the sleeve 850 and to the outside environment where its proximal end may be accessed to insert one or more catheters and/or other tools.

Figure 18:
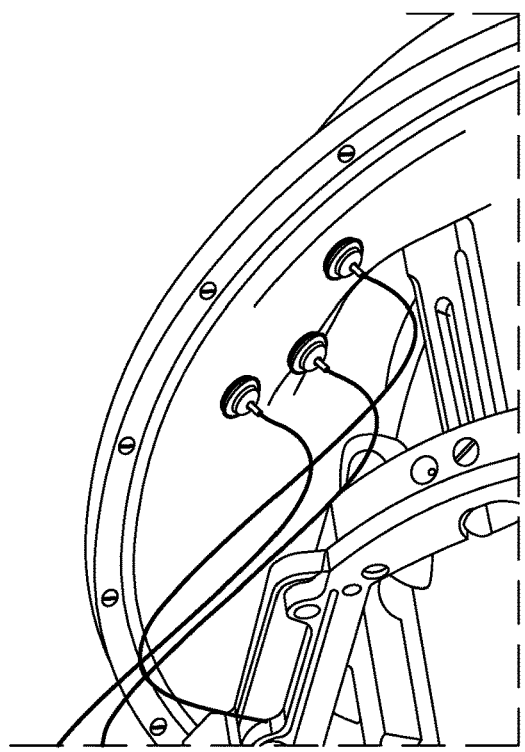
FIG. 18 illustrates a section of a cranial diaphragm with a plurality of access port assemblies installed in accordance with another embodiment.
Figure 19:
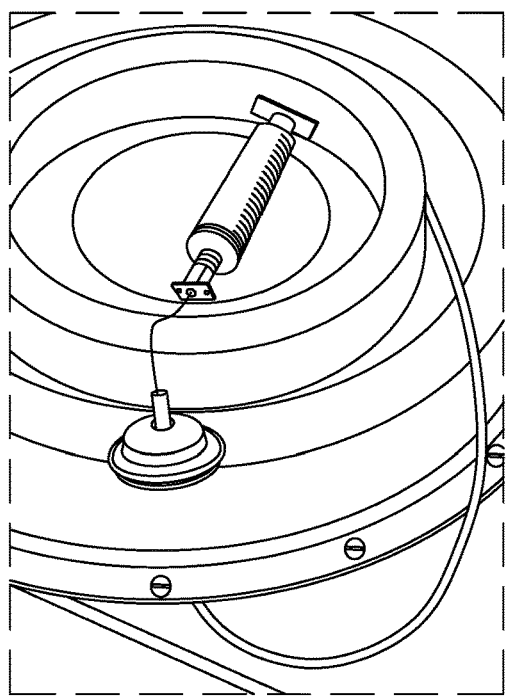
FIG. 19 illustrates a cranial diaphragm with an access port coupled to a syringe in accordance with an embodiment.
Figure 20:
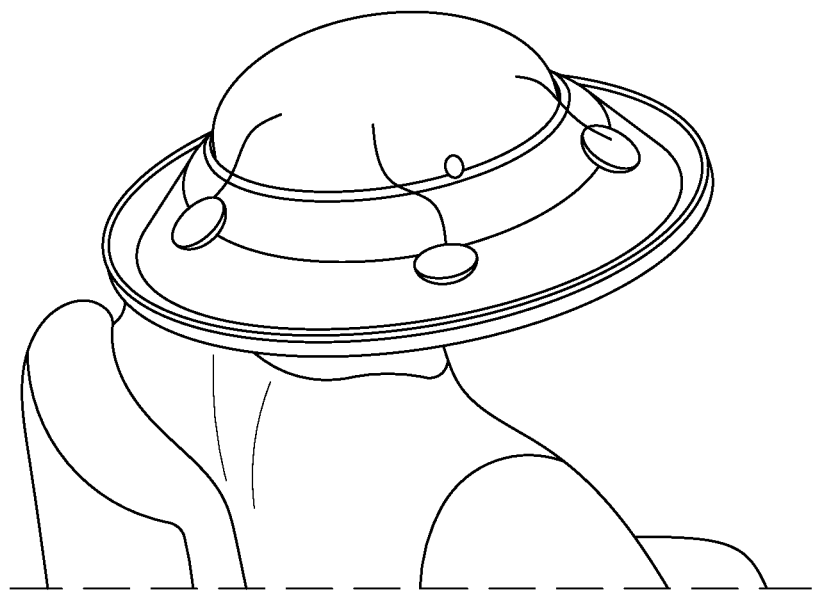
FIG. 20 illustrates a perspective top view of a cranial diaphragm with a plurality of access port assemblies installed in accordance with another embodiment.

As shown in FIGS. 17 through 20, the access ports secured to the diaphragm membrane can be of any suitable size. For instance, a smaller configuration of the access port, as shown in FIG. 18, can be used to tunnel out EEG leads. FIG. 19 illustrates a syringe coupled to an access port to instill an amount of medication. A plurality of access ports may be secured to any suitable position on the diaphragm membrane, as desired. For instance, a group of access ports may be secured proximate each other as in FIG. 18 or a plurality of access ports can be spaced radially around the cranial diaphragm, as shown in FIG. 20. The relatively simple configuration of the access ports allows positioning of the access ports anywhere along the diaphragm membrane, as needed. Moreover, it is to be appreciated that the access port configuration shown herein is merely an example configuration and any suitable structure, device, or system can be used as an access port so long as the configuration provides liquid tight access for a guide tube through a diaphragm membrane. In each of the systems disclosed herein, once a guide tube has been placed and the patient introduced into an MRgFUS device, the guide tube is pushed through an access port to the external environment. A surgeon can then insert a treatment catheter, such as a suction catheter, or other tool for treatment of the target body (e.g., hematoma) via the guide tube to deliver its distal end proximate the target body. Insertion and positioning of the catheter and/or tool is carried out via MRI guidance as desired relative to the body. At the same time, it is possible to re-confirm proper placement of the distal end of the guide tube. If adjustments to the guide tube or to the catheter fed therethrough are appropriate to reposition either, such adjustments can be made by the surgeon under real-time MRI guidance as is conventional, but now within the MRgFUS device. Once hematoma triangulation and catheter placement have been established/confirmed, the transducer assembly can be actuated to deliver a targeted dose of ultrasound energy to the body in order to liquefy it. Liquefied material then is aspirated via the emplaced catheter, which is fed via the guide tube, and confirmed via MRI periodically or in real-time. As liquefied thrombotic material is drained, adjustments in position of the distal end of the catheter can be made, as well as additional targeted doses of ultrasound energy delivered, based on MRI imaging as it evolves through liquefaction and drainage.

In addition to lateral repositioning, the depth of the catheter also may be adjusted based on MRI image guidance; for example, by advancing and/or withdrawing the catheter via the guide tube along its insertion axis as needed. Withdrawal to reposition the distal end of the catheter at a shallower location might be achieved simply by mechanically pulling the catheter from outside the MRgFUS device, which will result in it being withdrawn along its insertion pathway through the guide tube and from the patient's cranium. Regarding advancement, similar adjustment can be achieved by physically pushing the catheter through the guide tube along its insertion axis.

There are two imaging activities that are essential for the success of this program: (1) where is the location of the catheter (and its tip) in relation to the hematoma; and (2) what portions of the clot have become liquid and which remain solid. As catheters are generally MRI-black on all sequences (contains no mobile protons), alternative ways need to be optimized to reliably identify their location, which we will undertake. This might also entail conducting a scan with contrast agents within the middle of the catheter. Imaging characteristics of liquid blood vs clotted blood can be strikingly different on various sequences, and we will optimize scan parameters to accentuate this difference. This imaging may also entail a thermography sequence to identify the temperature of the clot during sonication. Ideally these sequences could be run in real time during sonication, and thereby provide real-time feedback about efficacy, and positioning. If optimized, after one sonication the catheter could be repositioned from a liquefied clot into a non-liquefied portion, and the process repeated. The images might be rendered into a 3D model that is displayed on the console or even in a VR space to help guide the treatment. It may be desirable to have a coordinate-based system that directs the position or suggests manual adjustments for the position of the catheter in space.

Figure 21:
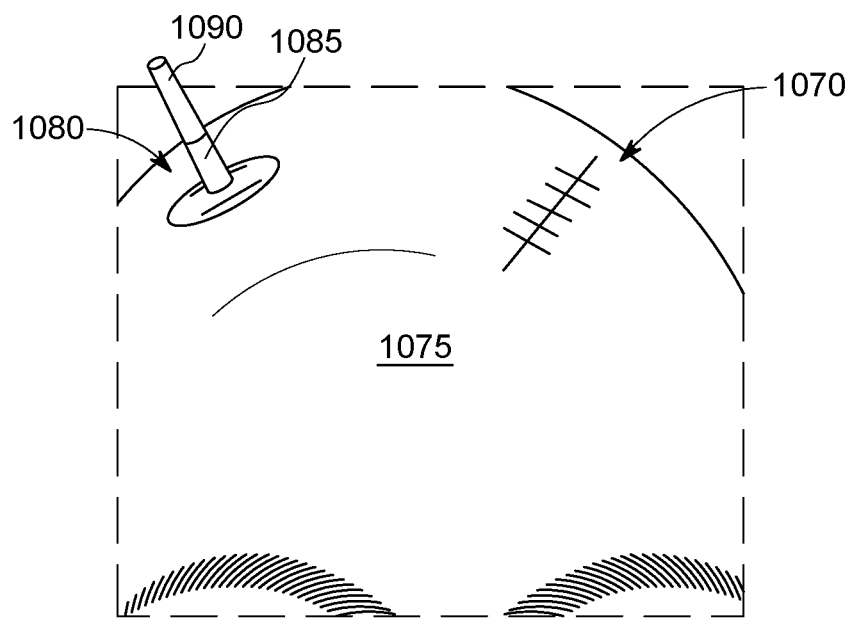
FIG. 21 illustrates an example of a guide tube tunneled under a patient's scalp in accordance with an embodiment.

Guide tubes can be placed and left in position for extended periods of time. The use of a guide tube allows for easy replacement of catheters that may become clogged and use of various tools during treatment. FIG. 21 illustrates an example of tunneling a guide tube 1090 beneath a patient's scalp 1075. As discussed above, an incision is made in the scalp and then an opening is provided through the skull. The guide tube 1090 is provided through the opening to a desired depth and then secured to the skull bone, such as via a balloon member. A proximal end of the guide tube 1090 can then be tunneled under the scalp to exit at a remote location (e.g., location 1080) so that the initial incision site 1070 can be closed. By closing the initial incision site, infection at the site is mitigated and contamination of the cooling liquid used in the MRgFUS system is prevented. The exit location 1080 for the guide tube 1090 can be positioned at a location within the jacket defined by a transducer assembly, in which case the guide tube 1090 is passed through an access port. However, the guide tube 1090 may also be tunneled to an exit location outside of the MRgFUS system, or in other words, outside of the cooling liquid bath. In both cases, a liquid tight anchor or sealing device 1085 can be provided at the exit location 1080 to support the guide tube 1090 and seal the opening from the liquid bath or the environment.

Figure 22:
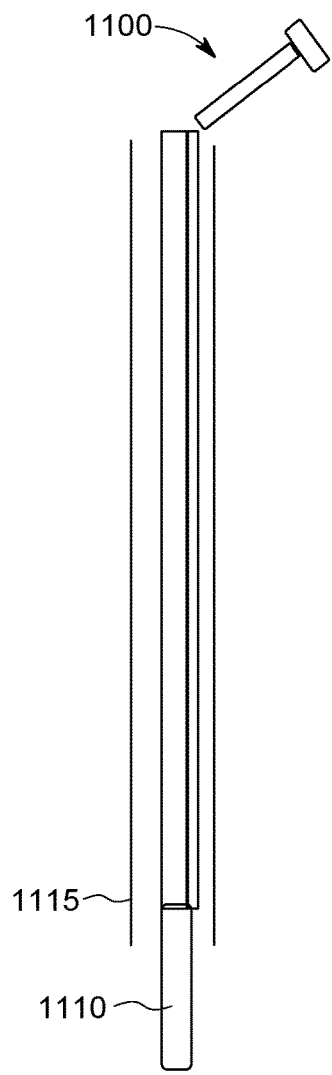
FIG. 22 illustrates an example of a first tool that can be used with a guide tube assembly in accordance with an embodiment.
Figure 23:
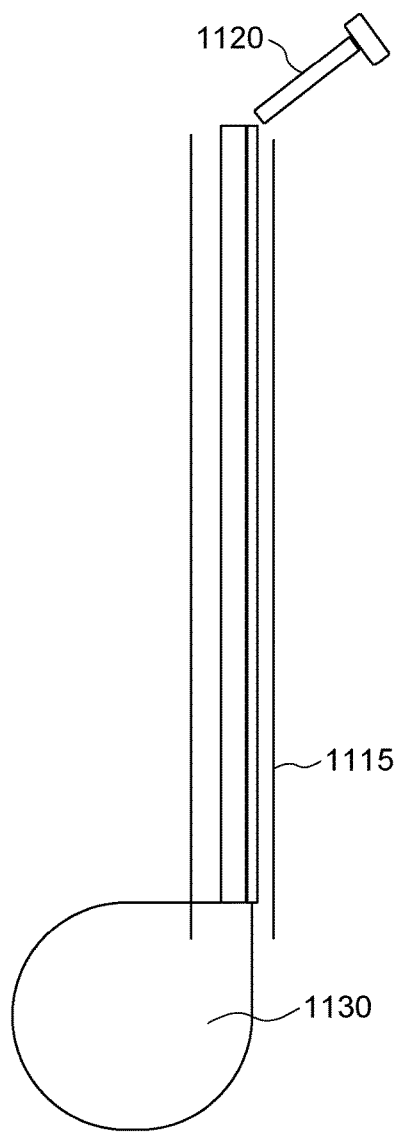
FIG. 23 illustrates an example of another tool that can be used with a guide tube assembly in accordance with an embodiment.
Figure 24:
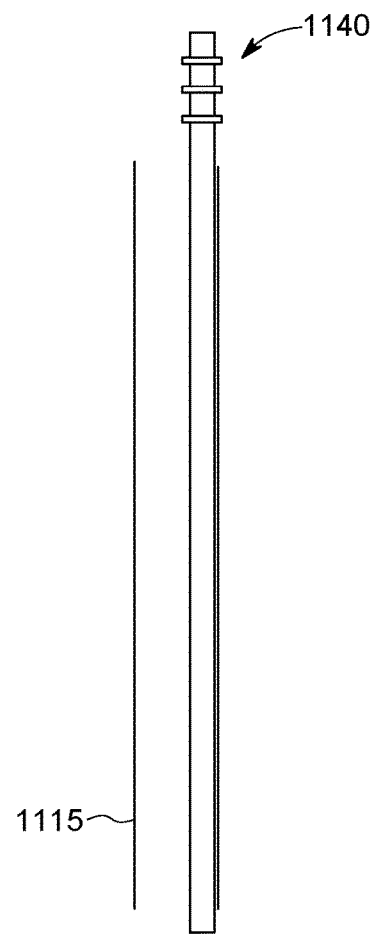
FIG. 24 illustrates an example of another tool that can be used with a guide tube assembly in accordance with an embodiment.

It is to be appreciated that various tools and/or instruments can be used in connection with the guide tube assembly described herein. For instance, as illustrated in FIG. 22, a syringe 1100 can be used to dispense an agent, such as flowseel or definity, preloaded at a tip portion 1110. The syringe 1100 can actuate a plunger and/or wires extending through the guide tube 1115 to release the agent. FIG. 23 illustrates another example in which a balloon 1130 is positioned through and extends past a distal end of the guide tube 1115. A syringe 1120 or other actuation device can be coupled to the balloon 1130 to inject a fluid and/or air to inflate the balloon 1130. This can be employed as a tamponade if active bleeding is encountered. FIG. 24 illustrates an intracranial pressure monitor transducer 1140 or other pressure monitor that can be provided through the guide tube 1115 and used as an early warning of increasing pressure. Moreover, any suitable catheter configuration can be used with the guide tube assembly disclosed herein. For instance, a telescoping catheter, such as the catheter developed by Route 92 Medical of San Mateo, California, can be used.

As previously described, one or more guidewires or navigation tools can be employed for assisting in the positioning and/or repositioning of the distal end of the catheter. The guidewires, if used during MRI imaging, must be suitable to mitigate imaging artifacts that could obscure the surgical field or create magnetic interactions resulting from ferromagnetic materials, which could damage both the patient and the MRI machine. Accordingly, the wires used to guide the catheter may be composed of nitinol, a nickel-titanium alloy that has been shown to be generally safe and not disruptive under MRI. However, depending on the strength of the MRI device (i.e. the magnetic field that it generates), it is possible that nitinol components or guidewires of a catheter may produce undesirable imaging artifacts. In that case, it may be appropriate to utilize instead rigid or semi-rigid plastic or fiberglass strands as guidewires to manipulate the distal end of a repositionable catheter to direct it to desired locations. These guidewires may be curved to improve steerability.

Figure 25:
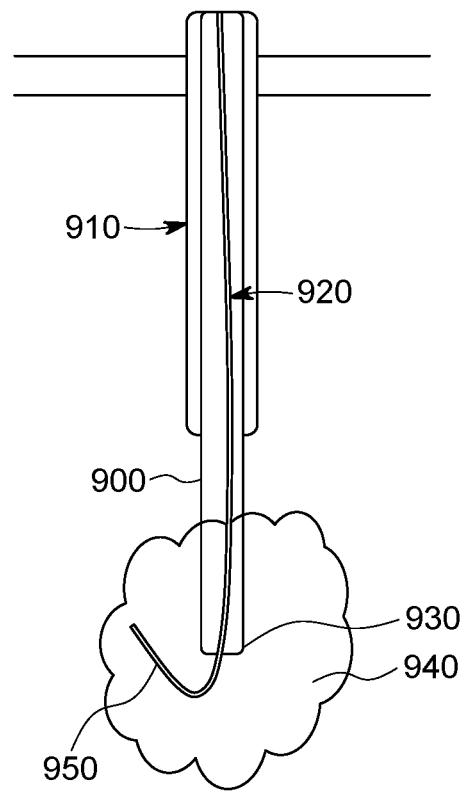
FIG. 25 illustrates a cross sectional schematic diagram of a catheter in accordance with an embodiment.

FIGS. 25 through 31 illustrate the use of smaller aspiration catheters that can be used to reach a hematoma. FIG. 25 illustrates a cross sectional schematic diagram of a catheter 900 according to one example. The catheter 900 is positioned through a guide tube 910, as described herein. A smaller aspiration catheter 920 extends through the catheter 900 to facilitate positioning of a distal end 930 of the catheter 900 proximate a hematoma 940. A tip portion 950 of the aspiration catheter 920 can include a J-shaped curve or any other desired shape to improve reachability of the aspiration catheter 920 within the hematoma. In addition, it may be necessary to insert catheters with small distal balloons attached to create a cavity in the clot and then deliver an agent such as Definity or tPA through the same catheter via a side channel.

Figure 26:
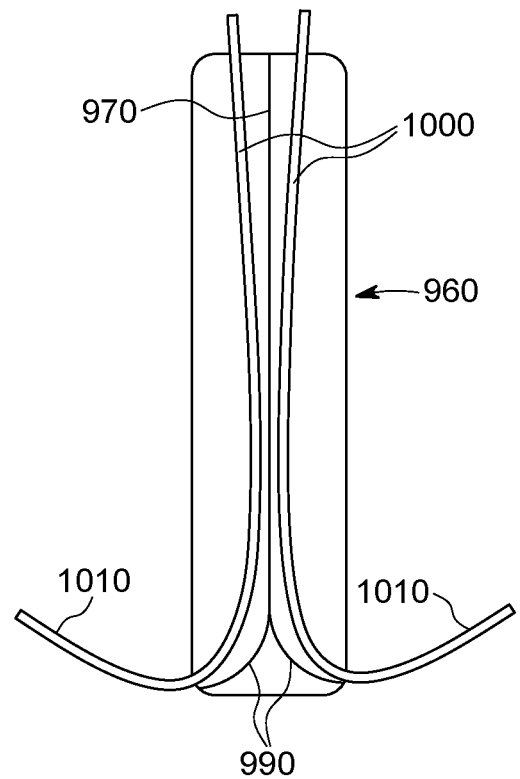
FIG. 26 illustrates a cross sectional schematic diagram of a multi-chambered catheter in accordance with another embodiment.
Figure 27:
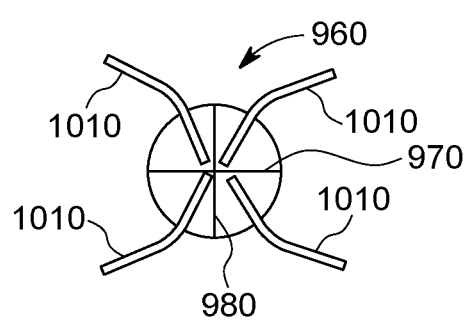
FIG. 27 illustrates a bottom view of the multi-chambered catheter illustrated in FIG. 26.

FIGS. 26 and 27 illustrate an example of a multi-chambered catheter that can be employed. FIG. 26 illustrates a longitudinal cross section of a catheter 960 having four chambers; and FIG. 27 illustrates a distal end view of the same catheter 960. The chambers are formed by two intersecting longitudinal walls or dividers 970, 980 extending the length of the catheter 960 and thereby dividing the catheter 960 into four substantially equal chambers. Smaller aspiration catheters 1000 can be provided through the chambers for facilitating aspiration of the liquified hematoma. In order to facilitate aspiration of a larger area of the hematoma, each of the chambers can have a curved base portion 990. When the aspiration catheter 1000 is provided through catheter 960, the curved base portion 990 projects a distal end 1010 of the aspiration catheter 1000 along the curve. Thus, by controlling the curve of the base portion 990, a larger area of the hematoma can be reached during aspiration. One or more of the chambers can also be used to deliver an agent, as will be discussed in more detail below.

Figure 28:
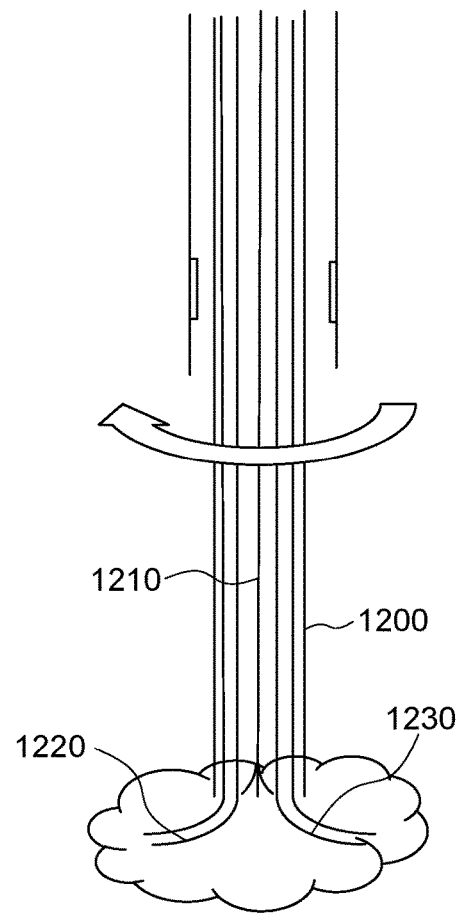
FIG. 28 illustrates a cross sectional schematic diagram of another multi-chambered catheter in accordance with another embodiment.
Figure 29A:
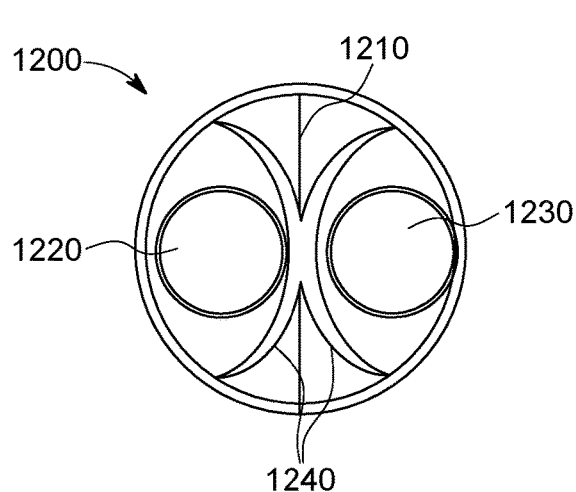
FIG. 29A illustrates a bottom view of the multi-chambered catheter illustrated in FIG. 28 as oriented in a first direction.
Figure 29B:
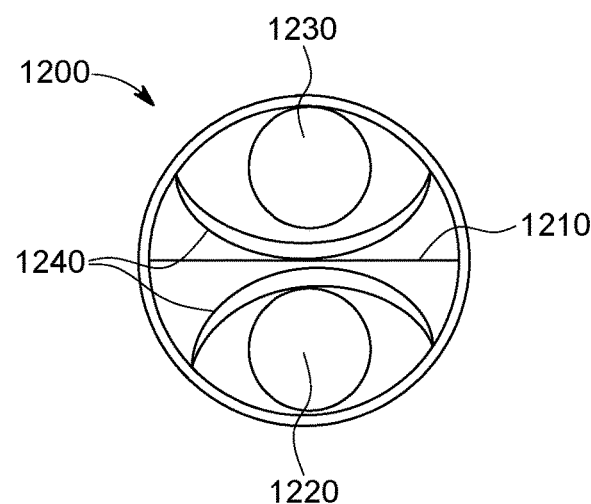
FIG. 29B illustrates a bottom view of the multi-chambered catheter illustrated in FIG. 28 as oriented in a second direction.
Figure 30:
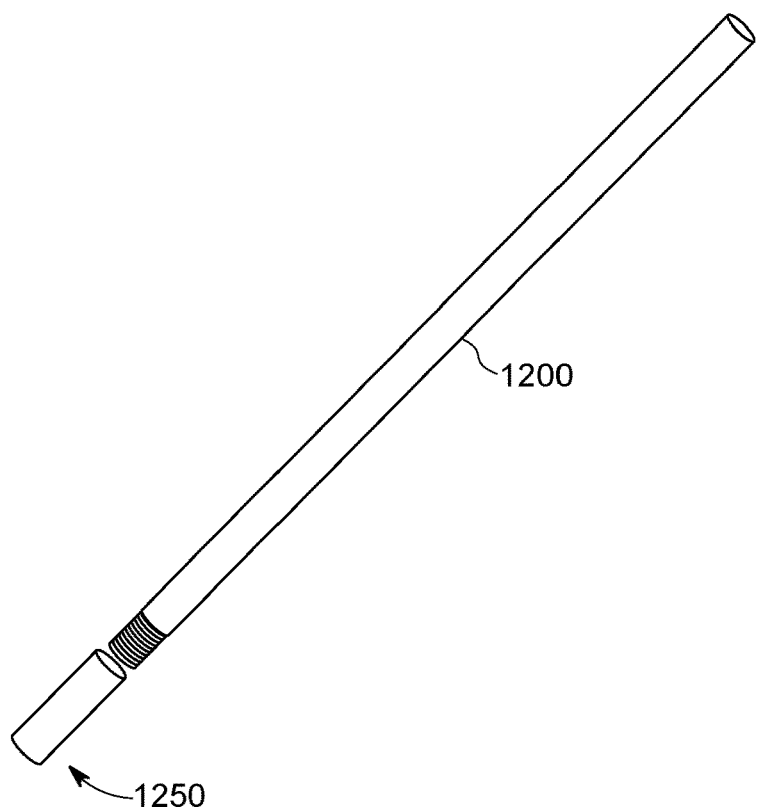
FIG. 30 illustrates an exploded perspective view of an example catheter assembly in accordance with an embodiment.
Figure 31:
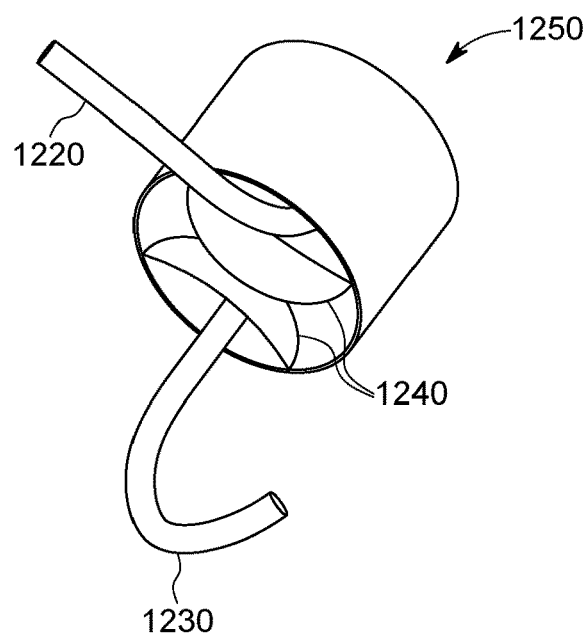
FIG. 31 illustrates a perspective view of an end attachment for a catheter assembly in accordance with an embodiment.

FIGS. 28-31 illustrate another example of a multi-chambered catheter in accordance with an embodiment. FIG. 28 illustrates a longitudinal cross section of a catheter 1200 having two chambers; and FIGS. 29A and 29B illustrate distal end views of the same catheter 1200. The chambers are formed by one longitudinal wall or divider 1210 extending the length of the catheter 1200 and thereby dividing the catheter 1200 into two substantially equal chambers. Smaller aspiration catheters 1220, 1230 can be provided through the chambers for facilitating aspiration of the liquified hematoma. As above, to facilitate aspiration of a larger area of the hematoma, each of the chambers can have a curved base portion 1240. When the aspiration catheters 1220, 1230 are provided through catheter 1200, the curved base portions 1240 project distal ends of the aspiration catheters 1220, 1230 along the curves. Thus, by controlling the curves 1240, a larger area of the hematoma can be reached during aspiration. Additionally, a larger area can be reached by rotation of the catheter 1220. FIG. 29A illustrates the catheter in a first position and FIG. 29B illustrates the catheter after a 90-degree counterclockwise rotation. Thus, using a two-chambered catheter and a 90-degree rotation can cover the same area as a four-chambered catheter as described herein. As shown in FIGS. 30 and 31, the curved base portions 1240 can be provided as an attachment 1250 that can be threaded or otherwise secured to the end of the catheter 1200. One or more of the chambers can also be used to deliver an agent, as will be discussed in more detail below.

A clotted hematoma can be liquefied in at least two ways using ultrasound. Initially, when a patient presents with symptoms indicative of a clot in the brain, such as an acute onset headache and right sided weakness, an image is acquired of the brain. The image can be acquired via CT, MRI, or any other suitable imaging system. Upon finding a deep-seated hemorrhage in the imaging results, a surgeon recommends how to best liquify and aspirate the clot. If the clot is located in a small central location of the brain, the surgeon may decide to use thermal lysis. Here, ultrasound energy delivers sufficient internal energy to the thrombotic material to reach a temperature threshold causing liquefaction; or via cavitation, where sonication delivers sufficient mechanical energy to disrupt the hematoma and mechanically disrupt thrombin to liquefy it. During this process, referred to as High Intensity Focused Ultrasound (HIFU), the ultrasonic energy is delivered at a higher frequency, such as 660 kHz, using low power for a long duration. It may not be desired to deliver any therapeutic agents to the hematoma prior to sonication during thermal lysis.

If the clot is large and/or located in a lateral location in the brain, the surgeon may decide to use mechanical lysis. In this situation, it may be desirable to deliver a cavitation-nucleation agent such as Definity®, which is an FDA-approved contrast agent. This agent has been shown to yield microbubbles that can be agitated via cavitation under ultrasound to deliver mechanical work. It was found that use of such an agent enhances liquification of the clot. A thrombolytic agent such as tPA could be added for synergistic effect. This or another suitable nucleation agent may be delivered via the catheter, previously emplaced with the hematoma. If desired, the catheter can be repositioned to distribute the nucleation agent at locations throughout the hematoma space under MM-image guidance. During this process, referred to as Low Intensity Focused Ultrasound (LIFU), the ultrasonic energy is delivered at lower frequency, such as 220 kHz, using high power for a short duration. In practice, whether via thermal denaturation or mechanical disruption, the hematoma can be liquefied via successive doses of targeted ultrasound radiation, followed by or contemporaneous with suction aspiration via the catheter to evacuate liquefied material. The target focus of sonication as well as the placement of the catheter distal end both can be adjusted in real time, or successively with intermediate MRI imaging, to liquefy and evacuate clot material.

Although embodiments described herein are made with reference to example embodiments, it should be appreciated by those skilled in the art that various modifications are well within the scope and spirit of this disclosure. The foregoing system and methods have been disclosed in the context of liquefying and aspirating a clotted deep-brain hematoma. However, it will be appreciated that other deep-brain interventions may be practiced using the disclosed system and methods. Therefore, the scope of the example embodiments is not limited herein. For example, in certain instances it may be desirable to combine targeted ultrasound therapy with deep-brain electrical stimulation to evaluate and treat epilepsy, or other neurologic disorders. In this scenario, a guide tube may be placed as described above to provide a conduit for delivering a deep-brain electrode to a desired position within the patient, in order to supply targeted electrical stimulation in combination with delivery targeted ultrasound energy. Also, multiple guide tubes as described above can be placed, for example passing through multiple access ports, in order to deliver catheter and/or tool access to different deep-brain positions, or to provide two or more catheters or tools in the same vicinity, e.g. to perform MM-guided microsurgery in conjunction with targeted sonification treatment. In other examples, the blood brain barrier may be opened and chemotherapy, immunotherapy, gene therapies or other therapeutic agents could be delivered to a body or region of interest, such as an abscess, infection, an area damaged by stroke. The disclosure is intended to include all such modifications and alterations disclosed herein or ascertainable herefrom by persons of ordinary skill in the art without undue experimentation.

The invention claimed is:

1. A method of treatment comprising:
    configuring a system for facilitating magnetic resonance-guided focused ultrasound aspiration to sonicate a body within an organ of a patient, the system comprising:
    a transducer assembly comprising an array of ultrasound transducers adapted to deliver ultrasound energy, said transducer assembly at least partially defining a substantially liquid-tight jacket adapted to contain a fluid medium in order to conduct ultrasound waves; and
    an access port adapted to accommodate therethrough a guide tube emerging from said jacket, said guide tube configured to permit passage of a catheter therethrough such that the catheter may be positioned adjacent to the body; and
    sonicating the body with ultrasound energy supplied by at least one of the array of transducers of the system, thereby liquefying the body to produce liquified material; and
    aspirating the liquified material via the catheter;
    wherein said liquid tight jacket has been applied against and forms a seal with the patient such that said fluid medium is confined between the jacket and the patient, wherein both sonication of the body and positioning of the catheter adjacent thereto are assisted via image guidance, wherein said guide tube is made exclusively of substantially non-ferromagnetic materials.

2. The method of claim 1, wherein the catheter is positioned adjacent to the body using CT imaging prior to sonicating the body, and wherein during sonication, MRI imaging is used to monitor the aspiration of the liquified material.

3. The method of claim 1, wherein real-time image guidance is used during sonication to reposition the catheter adjacent the liquified material as the liquified material is aspirated.

4. The method of claim 1, further comprising delivering a cavitation nucleation agent to the body to enhance liquification of the body.

5. The method of claim 1, wherein high intensity focused ultrasound energy is used to produce the liquified material.

6. The method of claim 1, wherein low intensity focused ultrasound energy is used to produce the liquified material.

7. The method of claim 1, said body being a deep-brain hematoma.

8. The method of claim 7, wherein the catheter is positioned adjacent to the hematoma prior to sonicating the hematoma and wherein the catheter is adjacent to the hematoma during sonication thereof.

9. The method of claim 7, wherein both sonication of the hematoma and positioning the catheter adjacent thereto are assisted via MRI-image guidance.

10. A system to facilitate magnetic resonance-guided focused ultrasound aspiration comprising:
   a transducer assembly comprising an array of ultrasound transducers adapted to deliver ultrasound energy, said transducer assembly at least partially defining a substantially liquid-tight jacket adapted to contain a fluid medium in order to conduct ultrasound waves; and
   an access port adapted to accommodate therethrough a guide tube emerging from said jacket, said guide tube configured to permit passage of a catheter therethrough;
   wherein said guide tube is made exclusively of substantially non-ferromagnetic materials.

11. The system of claim 10, said substantially non-ferromagnetic materials comprising one or more of plastic, fiberglass, nitinol.

12. The system of claim 10, the transducer assembly have a substantially hemispherical shape and configured to surround a portion of a head of a patient.

13. The system of claim 10, further comprising said catheter accommodated through said guide tube.

14. The system of claim 13, wherein the catheter is a multi-chambered catheter configured to receive at least one aspiration catheter therethrough.

15. The system of claim 10, further comprising a diaphragm helping to define said substantially liquid-tight jacket.

16. The system of claim 15, further comprising an access ring interposed between said transducer assembly and said diaphragm and also helping to define said substantially liquid-tight jacket, the access ring comprising the access port adapted to accommodate said guide tube therethrough.

17. The system of claim 10, further comprising a diaphragm secured to the transducer assembly, wherein the access port is provided through a membrane of the diaphragm.

18. The system of claim 17, wherein the access port comprises:
   a first body and a first gasket coupled to a first surface of the membrane;
   a second body and a second gasket coupled to a second opposing surface of the membrane; and
   a sleeve extending through the first body, the first gasket, the second body, the second gasket, and the membrane.

19. The system of claim 10, further comprising a diaphragm and an access ring, the access ring having a first side secured to the transducer assembly and a second side secured to the diaphragm.

20. The system of claim 19, wherein the access ring includes a substantially circular frame and a plurality of access ports distributed about a circumference of the frame.

21. The system of claim 10, further comprising an inflatable member, the guide tube extending through an inner diameter of the inflatable member.

22. The system of claim 21 wherein the
   inflatable member is coupled to the guide tube, the inflatable member being slidably adjustable along the length of the guide tube, the inflatable member configured to expand radially inwardly and outwardly.

23. The system of claim 22, further comprising a secondary tube coupled to the guide tube, the secondary tube configured to receive a navigation tool therethrough.

24. The system of claim 22, further comprising a communication tube coupled to the inflatable member for inflation and deflation of the inflatable member.

25. The system of claim 22, further comprising a dial lock coupled to one end of the guide tube.

26. A system to facilitate magnetic resonance-guided focused ultrasound aspiration comprising:
   a transducer assembly comprising an array of ultrasound transducers adapted to deliver ultrasound energy, said transducer assembly at least partially defining a substantially liquid-tight jacket adapted to contain a fluid medium in order to conduct ultrasound waves;
   an access port adapted to accommodate therethrough a guide tube emerging from said jacket; and
   a catheter accommodated through said guide tube;
   wherein said guide tube is made exclusively of substantially non-ferromagnetic materials.

27. A system to facilitate magnetic resonance-guided focused ultrasound aspiration comprising:
   a transducer assembly comprising an array of ultrasound transducers adapted to deliver ultrasound energy, said transducer assembly at least partially defining a substantially liquid-tight jacket adapted to contain a fluid medium in order to conduct ultrasound waves;
   a diaphragm secured to the transducer assembly; and
   an access port provided through a membrane of the diaphragm and adapted to accommodate therethrough a guide tube emerging from said jacket;
   wherein said guide tube is made exclusively of substantially non-ferromagnetic materials.

\* \* \* \* \*